(12) United States Patent
McFann et al.

(10) Patent No.: US 7,867,964 B2
(45) Date of Patent: Jan. 11, 2011

(54) SHAPED TOILET BARS

(75) Inventors: Gregory Jay McFann, North Bergen, NJ (US); Manoj Misra, Southington, CT (US); Peter Daniel Kaplan, Montclair, NJ (US); George Giugno, Derby, CT (US); Robert Paul Velthuizen, Trumbull, CT (US)

(73) Assignee: Conopco, Inc., Englewood Cliffs, NJ (US)

(*) Notice: Subject to any disclaimer, the term of this patent is extended or adjusted under 35 U.S.C. 154(b) by 179 days.

(21) Appl. No.: 12/283,840

(22) Filed: Sep. 16, 2008

(65) Prior Publication Data

US 2010/0069277 A1 Mar. 18, 2010

(51) Int. Cl.
*A61K 7/50* (2006.01)

(52) U.S. Cl. ....................... 510/141; 510/151; 510/152; 510/153; 510/155

(58) Field of Classification Search ....................... None
See application file for complete search history.

(56) References Cited

U.S. PATENT DOCUMENTS

| | | | |
|---|---|---|---|
| 2,704,279 A | 3/1955 | Franklin | |
| 3,847,527 A | 11/1974 | Fischer | |
| 3,857,662 A | 12/1974 | Ratz | |
| 4,396,521 A | 8/1983 | Borrello | |
| 4,705,644 A | 11/1987 | Barone et al. | |
| 5,217,639 A * | 6/1993 | Mottola | 510/146 |
| 5,227,086 A | 7/1993 | Kacher et al. | |
| 5,229,059 A | 7/1993 | Divone, Sr. et al. | |
| 5,256,013 A | 10/1993 | Divone, Sr. et al. | |
| 5,284,598 A | 2/1994 | Subramanyam et al. | |
| 5,315,905 A | 5/1994 | Karavadra | |
| 5,394,605 A | 3/1995 | Fattori et al. | |
| 5,703,025 A | 12/1997 | Zyngier et al. | |
| 5,916,856 A | 6/1999 | Massaro et al. | |
| 5,952,289 A | 9/1999 | Wise et al. | |
| 6,057,275 A | 5/2000 | Fair et al. | |
| 6,147,040 A | 11/2000 | Van der Hagen | |
| 6,362,145 B1 | 3/2002 | Littau et al. | |
| 6,395,692 B1 | 5/2002 | Jaworski et al. | |
| 6,533,979 B1 | 3/2003 | Lee | |
| 2001/0039254 A1 | 11/2001 | Browne et al. | |
| 2003/0074795 A1 | 4/2003 | Marshall et al. | |
| 2005/0084480 A1 | 4/2005 | Bout et al. | |
| 2005/0107273 A1 | 5/2005 | Hourigan | |
| 2006/0002883 A1 | 1/2006 | Morikis et al. | |

FOREIGN PATENT DOCUMENTS

GB 989 007 A 4/1965

(Continued)

OTHER PUBLICATIONS

International Search Report. PCT/EP2009/061734, mailed Mar. 23, 2010, 6 pp.

*Primary Examiner*—Necholus Ogden, Jr.
(74) *Attorney, Agent, or Firm*—Alan A. Bornstein

(57) ABSTRACT

Intricately shaped toilet bars with specific compositions and plasticity properties can be advantageously manufactured via three dimensional cutting. Such cut bars are characterized by specific surface profiles and topographic features. Intricately shaped toilet bars with a wide range of formulations for enhanced skin treatment can be thus economically and reliably manufactured.

20 Claims, 15 Drawing Sheets

FOREIGN PATENT DOCUMENTS

| | | | |
|---|---|---|---|
| GB | 1 242 886 | A | 8/1971 |
| GB | 1 462 456 | | 7/1974 |
| GB | 1 437 323 | A | 5/1976 |
| WO | 96/04360 | A1 | 2/1996 |
| WO | 03/086111 | | 10/2003 |

* cited by examiner

SHAPED TOILET BARS

BACKGROUND OF THE INVENTION

1. Field of the Invention

The present invention relates to a toilet bar suitable for cleansing. In particular, it relates to a toilet bar that has a specific formulation and plasticity or surface properties.

2. The Related Art

Toilet bars are well known for providing a wide range of skin care and cleansing benefits and are frequently made available to consumers in aesthetically pleasing shapes. Toilet bars that contain high levels of soap and synthetic surfactants are excellent for cleaning and usually have sufficient hardness to be economically extruded into a billet and stamped into a final attractive shape. Stamping, however, does not provide for creating intricate three dimensional shapes. Toilet bars that are transparent or translucent and/or contain high levels of components that are liquid at room temperature are usually too soft to be stamped and must usually be cast in a shaped mold or frame from a flowable feedstock. Casting also has limitations regarding the creation of intricate shapes. The cast bar will often have at least one flat surface upon hardening and will thus limit the choice of shape of the finished bar unless further process steps are employed to shape the flat surface(s). Additional steps will add to the complexity and cost of making such bars. Manufacturers have sought to provide to the consumer aesthetically pleasing shaped toilet bars that are shaped on their entire surface while attempting to meet a wide range of skin conditioning qualities, manufacturing and formulation constraints. A brief representation of the prior art is set forth below.

U.S. Pat. No. 3,856,449 issued to Fisher on Dec. 24, 1974 discloses a wire trimmer for trimming soap extrusions to obtain improved surface finish for soap. The cut lines will all be parallel to the direction of motion of the extruded soap.

U.S. Pat. No. 5,083,486 issued to Allison et al. on Jan. 28, 1992 discloses a method and apparatus for trimming non-soap solid stick deodorants to provide for a protruding rounded deodorant stick in the container.

U.S. Pat. No. 6,024,967 issued to Fattori et al. on Feb. 15, 2000 discloses a method and apparatus for shaping a top surface of a non-soap antiperspirant or deodorant product to have a compound-curved shape using a plurality of cutting blades.

It has been discovered that three-dimensional shaping via cutting can be usefully employed to produce aesthetically pleasing bar shapes for specifically formulated toilet bars that unexpectedly possess a defined range of plasticity in order to produce a bar with an acceptable appearance (i.e. having minimal or no visually detectable surface defects such as cracks and gouges). Such plasticity can be quantified by the fracture initiation energy ($G_{ic}$) and the fracture energy parameter ($G_c$) from a three-point bending test described below. Moreover, a specific range of yield stress ($\sigma_y$) was also unexpectedly found to be an important property for preparing a bar with an acceptable appearance after cutting i.e. avoiding surface defects, as well as for generally efficient processing of the inventive bar. The inventive bar was discovered to have a distinctive striated topographic pattern compared to bars shaped by stamping or casting, and this striated pattern can be quantified using microscopic analysis techniques described below.

SUMMARY OF THE INVENTION

In one aspect of the invention is a shaped toilet bar including but not limited to:

a. about 10% to 60% by wt. of total non-soap anionic surfactant(s);
b. 0% to about 30% by wt. of fatty acid soap(s);
c. wherein the bar has a fracture initiation energy ($G_{ic}$) greater than 2 J/m$^2$.;
d. wherein the bar has a length extending along an x axis, a width extending along a y axis, and a thickness extending along a z axis, and the x, y and z axis are orthogonal to each other; and
e. wherein the bar has an exterior surface, wherein the exterior surface includes:
    i. a top surface, a bottom surface and a middle portion extending from the top to the bottom surface;
    ii. wherein the top surface has a first profile extending along the x axis, the bottom surface has a second profile extending along the y axis, and the middle portion has a third profile normal to the z axis;
    iii. each of said first, second and third profiles independently being either linear, curvilinear or having both linear and curvilinear elements;
    iv. wherein at least two of the first, second and third profiles are different; and
    v. wherein the maximum value of the standard deviations of a Directional Variation Array of surface striations of each of the top surface, bottom surface and middle portion of the bar is each greater than 0.64 calculated via the DVA surface imaging method.

In a second aspect of the invention is a shaped toilet bar including but not limited to:

a. about 5% to 40% by wt. of total non-soap anionic surfactant(s);
b. about 30% to 80% by wt. of fatty acid soap(s);
c. wherein the bar has a fracture initiation energy ($G_{ic}$) greater than 2 J/m$^2$.;
d. wherein the bar has a length extending along an x axis, a width extending along a y axis, and a thickness extending along a z axis, and the x, y and z axis are orthogonal to each other; and
e. wherein the bar has an exterior surface, wherein the exterior surface includes:
    i. a top surface, a bottom surface and a middle portion extending continuously from the top to the bottom surface,;
    ii. wherein the top surface has a first profile extending along the x axis, the bottom surface has a second profile extending along the y axis, and the middle portion has a third profile normal to the z axis;
    iii. each of said first, second and third profiles independently being either linear, curvilinear or having both linear and curvilinear elements;
    iv. wherein at least two of the first, second and third profiles are different; and
    v. wherein the maximum value of the standard deviations of a Directional Variation Array of surface striations of each of the top surface, bottom surface and middle portion of the bar is each greater than 0.64 calculated via the DVA surface imaging method.

In a third aspect of the invention is a shaped toilet bar including but not limited to:

a. 0% to about 10% by wt. of total non-soap anionic surfactant(s);

b. about 40% to 90% by wt. of fatty acid soap(s);

c. wherein the composition has a fracture initiation energy ($G_{ic}$) greater than 2 $J/m^2$;

d. wherein the bar has a length extending along an x axis, a width extending along a y axis, and a thickness extending along a z axis, and the x, y and z axis are orthogonal to each other; and e. wherein the bar has an exterior surface, wherein the exterior surface includes:

i. a top surface, a bottom surface and a middle portion extending continuously from the top to the bottom surface,;

ii. wherein the top surface has a first profile extending along the x axis, the bottom surface has a second profile extending along the y axis, and the middle portion has a third profile normal to the z axis;

iii. each of said first, second and third profiles independently being either linear, curvilinear or having both linear and curvilinear elements;

iv. wherein at least two of the first, second and third profiles are different; and v. wherein the maximum value of the standard deviations of a Directional Variation Array of surface striations of each of the top surface, bottom surface and middle portion of the bar is each greater than 0.64 calculated via the DVA surface imaging method.

In a fourth aspect of the invention is a shaped toilet bar including but not limited to:

a. 0 to about 40% by wt. of total non-soap anionic surfactant(s);

b. 0 to about 60% by wt. of fatty acid soap(s), provided that the sum of total non-soap anionic surfactants and fatty acid soaps is not 0;

c. about 10% to 50% by wt. of total mono and polyhydric alcohols;

d. wherein the composition has a fracture initiation energy ($G_{ic}$) greater than 2 $J/m^2$.;

e. wherein the bar has a length extending along an x axis, a width extending along a y axis, and a thickness extending along a z axis, and the x, y and z axis are orthogonal to each other; and f. wherein the bar has an exterior surface, wherein the exterior surface includes:

i. a top surface, a bottom surface and a middle portion extending from the top to the bottom surface;

ii. wherein the top surface has a first profile extending along the x axis, the bottom surface has a second profile extending along the y axis, and the middle portion has a third profile normal to the z axis;

iii. each of said first, second and third profiles independently being either linear, curvilinear or having both linear and curvilinear elements;

iv. wherein at least two of the first, second and third profiles are different; and v. wherein the maximum value of the standard deviations of a Directional Variation Array of surface striations of each of the top surface, bottom surface and middle portion of the bar is each greater than 0.64 calculated via the DVA surface imaging method.

DETAILED DESCRIPTION OF THE INVENTION

All publications and patent applications, patents, and other references mentioned herein are incorporated by reference in their entirety.

Figure 1A:
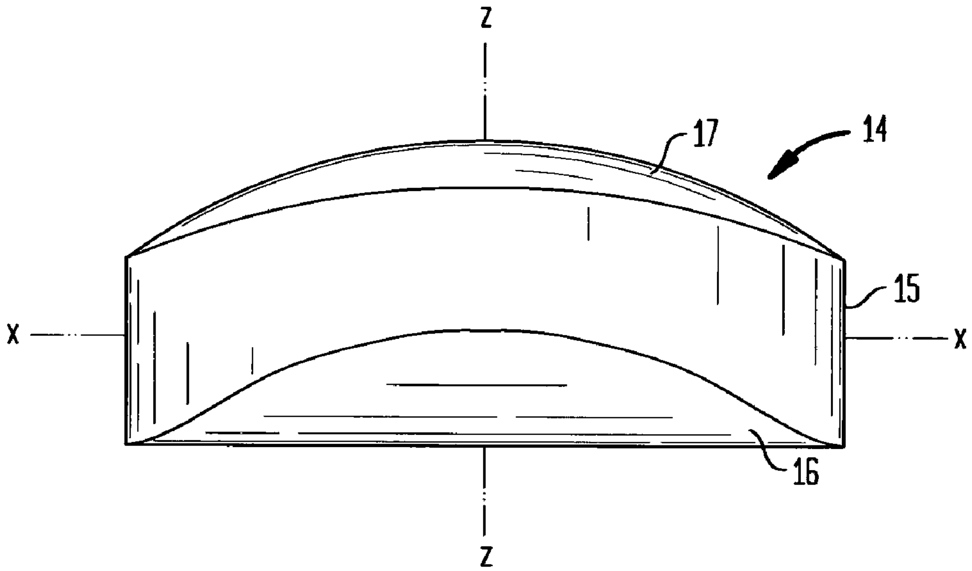
FIG. 1A is a side elevational view of an embodiment of an inventive bar.
Figure 1B:
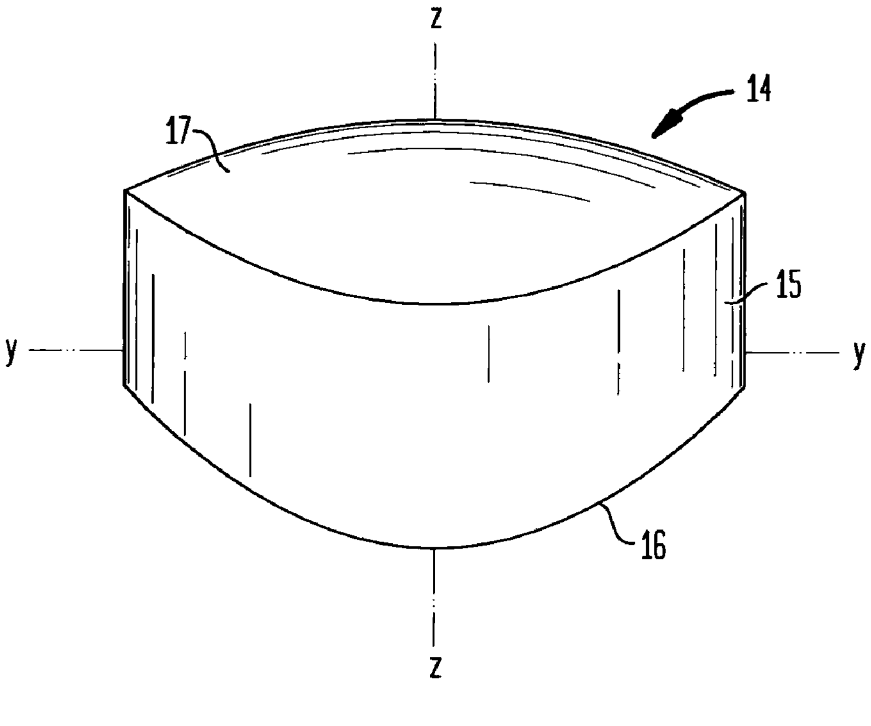
FIG. 1B is a side elevational view of the embodiment of the inventive bar depicted in FIG. 1A oriented at 90 degrees.
Figure 1C:
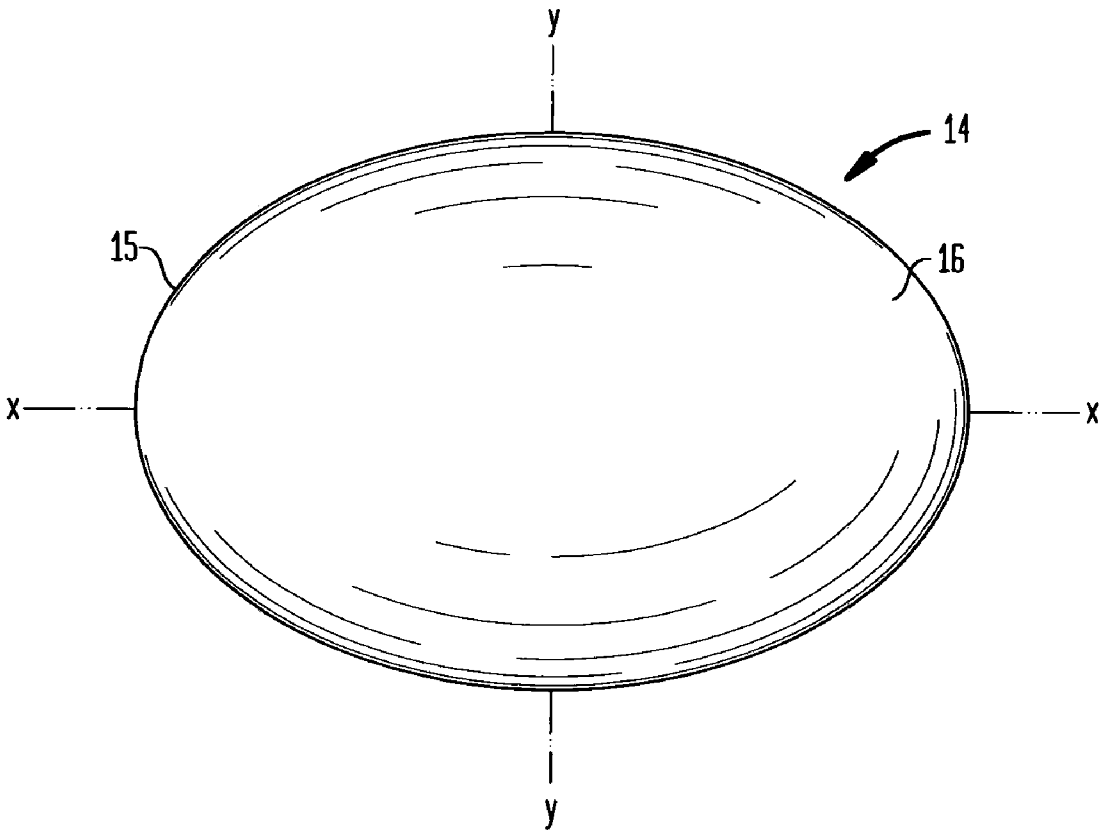
FIG. 1C is a bottom plan view of the embodiment of the inventive bar depicted in FIG. 1A.

Referring now to the drawings in which like figures represent like elements, FIGS. 1A to C depict different views defined by x, y, z coordinates of one embodiment of an inventive shaped bar 14 having a middle portion 15, a bottom surface 16 and a top surface 17. A first profile, i.e., perimeter, of the bar 14 extends along the length or x axis of the bar and is parallel with the XZ plane, A second profile of the bar extends along the width or y axis of the bar and is parallel with yz plane. A third profile of the bar is normal to the z axis of the bar and is parallel with the xy plane. Shaped profiles or surfaces are herein defined as curvilinear profiles or surfaces as opposed to flat profiles or surfaces.

In a first embodiment of the invention is a shaped toilet bar including but not limited to:

a. about 10% to 60% by wt. of total non-soap anionic surfactant(s) (preferably the minimum concentration is about 15, 20 or 25 and the maximum concentration is about 50 or 55% by wt. of total non-soap anionic surfactant(s));
b. 0% to about 30% by wt. of fatty acid soap(s) (preferably the maximum concentration is about 20 or 25% by wt. of a fatty acid soap);
c. wherein the bar has a fracture initiation energy ($G_{ic}$) greater than 2 $J/m^2$. (preferably the minimum fracture initiation energy has a lower limit of about 8, 12 or 16 and the maximum fracture initiation energy has an upper limit of about 24 or 20 $J/m^2$);
d. wherein the bar has a length extending along an x axis, a width extending along a y axis, and a thickness extending along a z axis, and the x, y and z axis are orthogonal to each other; and
e. wherein the bar has an exterior surface, wherein the exterior surface includes:
    i. a top surface, a bottom surface and a middle portion extending from the top to the bottom surface, (preferably wherein the each of the top surface, the middle portion and the bottom surface has the same composition);
    ii. wherein the top surface has a first profile extending along the x axis, the bottom surface has a second profile extending along the y axis, and the middle portion has a third profile normal to the z axis;
    iii. each of said first, second and third profiles independently being either linear, curvilinear or having both linear and curvilinear elements;
    iv. wherein at least two of the first, second and third profiles are different (preferably the first, second and third profiles are all different); and
    v. wherein the maximum value of the standard deviations of a Directional Variation Array of surface striations of each of the top surface, bottom surface and middle portion of the bar is each greater than 0.64 calculated via the DVA surface imaging method.

Optionally the first embodiment bar composition may contain 0 to about 10% by wt. of total amphoteric surfactant(s), 0 to about 10% by wt. of total nonionic surfactant(s), 0 to about 5% by wt. of total cationic surfactant(s), 0 to about 10% by wt. of total cationic polymer(s), about 5 to 30% by wt. of total hydrophobic structurant(s), about 5 to 40% by wt. of hydrophilic structurant(s), 0 to about 10% by wt. of total solvent(s), 0 to about 7% by wt. of total hydrophobic emollient(s) and 0 to about 7% by wt. of total humectant(s).

Preferably the first embodiment of the bar has a fracture energy ($G_c$) greater than about 25 $J/m^2$. More preferably the minimum fracture energy has a lower limit of about 100, 150 or 200 and the maximum fracture energy has an upper limit of about 300 or 250.

Advantageously the bar has a yield stress greater than about 100 kPa Preferably the maximum yield stress has an upper limit of about 600 kPa. Advantageously at least two of the first, second or third profiles of the bar have curvilinear profiles. Preferably the first, second and third profiles are all curvilinear.

In a second embodiment of the invention is a shaped toilet bar including but limited to:

a. about 5% to 40% by wt. of total non-soap anionic surfactant(s) (preferably the minimum concentration is about 7 or 10 and the maximum concentration is about 20 or 30% by wt. of total non-soap anionic surfactant(s));
b. about 30% to 80% by wt. of fatty acid soap(s) (preferably the minimum concentration is about 35 or 40 and the maximum concentration is about 60 or 70% by wt. of fatty acid soap(s));
c. wherein the bar has a fracture initiation energy ($G_{ic}$) greater than 2 $J/m^2$. (Preferably the minimum fracture initiation energy has a lower limit of about 8, 12 or 16 and the maximum fracture initiation energy has an upper limit of about 24 or 20) $J/m^2$;
d. wherein the bar has a length extending along an x axis, a width extending along a y axis, and a thickness extending along a z axis, and the x, y and z axis are orthogonal to each other; and
e. wherein the bar has an exterior surface, wherein the exterior surface includes:
    i. a top surface, a bottom surface and a middle portion extending continuously from the top to the bottom surface, (preferably wherein the each of the top surface, the middle portion and the bottom surface has the same composition);
    ii. wherein the top surface has a first profile extending along the x axis, the bottom surface has a second profile extending along the y axis, and the middle portion has a third profile normal to the z axis;
    iii. each of said first, second and third profiles independently being either linear, curvilinear or having both linear and curvilinear elements;
    iv. wherein at least two of the first, second and third profiles are different (preferably the first, second and third profiles are all different); and
    v. wherein the maximum value of the standard deviations of a Directional Variation Array of surface striations of each of the top surface, bottom surface and middle portion of the bar is each greater than 0.64 calculated via the DVA surface imaging method.

Optionally the second embodiment of the bar composition may contain 0 to about 10% by wt. of total amphoteric surfactant(s), 0 to about 7% by wt. of total nonionic surfactant(s), 0 to about 5% by wt. of total cationic surfactant(s), 0 to about 10% by wt. of total cationic polymer(s), 0 to about 10% by wt. of total hydrophobic structurant(s), 0 to 10% by wt. of hydrophilic structurant(s), 0 to about 10% by wt. of total solvent(s), 0 to about 7% by wt. of total hydrophobic emollient(s) and 0 to about 10% by wt. of total humectant(s).

Preferably the second embodiment toilet bar has a fracture energy ($G_c$) greater than about 25 $J/m^2$. Preferably the minimum fracture energy has a lower limit of about 100, 150 or 200 and the maximum fracture energy has an upper limit of about 300 or 250. Preferably the toilet bar has a yield stress at greater than about 100 kPa. Preferably the maximum yield stress has an upper limit of about 600. Advantageously at least two of the first, second or third profiles of the bar have curvilinear profiles. Preferably the first, second and third profiles are all curvilinear.

In a third embodiment of the invention is a shaped toilet bar including but not limited to:

a. 0% to about 10% by wt. of total non-soap anionic surfactant(s) (preferably the maximum concentration is about 5 or 7% by wt. of total non-soap anionic surfactant(s));
b. about 40% to 90% by wt. of fatty acid soap(s) (preferably the minimum concentration is about 50 or 60 and the maximum concentration is about 85 or 80% by wt. of fatty acid soap(s));
c. wherein the composition has a fracture initiation energy ($G_{ic}$) greater than 2 J/$m^2$. (Preferably the minimum fracture initiation energy has a lower limit of about 8, 12 or 16 and the maximum fracture initiation energy has an upper limit of about 24 or 20) J/$m^2$;
d. wherein the bar has a length extending along an x axis, a width extending along a y axis, and a thickness extending along a z axis, and the x, y and z axis are orthogonal to each other; and
e. wherein the bar has an exterior surface, wherein the exterior surface includes:
    i. a top surface, a bottom surface and a middle portion extending continuously from the top to the bottom surface, (preferably wherein the each of the top surface, the middle portion and the bottom surface has the same composition);
    ii. wherein the top surface has a first profile extending along the x axis, the bottom surface has a second profile extending along the y axis, and the middle portion has a third profile normal to the z axis;
    iii. each of said first, second and third profiles independently being either linear, curvilinear or having both linear and curvilinear elements;
    iv. wherein at least two of the first, second and third profiles are different (preferably the first, second and third profiles are all different); and
    v. wherein the maximum value of the standard deviations of a Directional Variation Array of surface striations of each of the top surface, bottom surface and middle portion of the bar is each greater than 0.64 calculated via the DVA surface imaging method.

Optionally the third embodiment of the bar composition may contain 0 to about 10% by wt. of total amphoteric surfactant(s), 0 to about 7% by wt. of total nonionic surfactant(s), 0 to about 5% by wt. of total cationic surfactant(s), 0 to about 10% by wt. of total cationic polymer(s), 0 to about 10% by wt. of total hydrophobic structurant(s), 0 to about 10% by wt. of hydrophilic structurant(s), 0 to about 15% by wt. of total solvent(s), 0 to about 7% by wt. of total hydrophobic emollient(s) and 0 to about 15% by wt. of total humectant(s).

Advantageously the third embodiment bar has a fracture energy ($G_c$) greater than about 25 J/$m^2$. Preferably the minimum fracture energy has a lower limit of about 100, 150 or 200 and the maximum fracture energy has an upper limit of about 300 or 250. Preferably the bar has a yield stress greater than about 100 kPa. Preferably the maximum yield stress has an upper limit of about 600. Preferably at least two of the first, second or third profiles of the bar have curvilinear profiles. Preferably the first, second and third profiles are all curvilinear.

In a fourth embodiment of the invention is a shaped toilet bar including but not limited to:

a. 0 to about 40% by wt. of total non-soap anionic surfactant(s); (preferably the minimum concentration is about 5, 10 or 20% by wt. and the maximum concentration is about 35, 30 or 25% by wt.)
b. 0 to about 60% by wt. of fatty acid soap(s), provided that the sum of total non-soap anionic surfactants and fatty acid soaps is not 0; (preferably the minimum concentration is about 10, 20 or 30% by wt. and the maximum concentration is about 55, 45 or 40% by wt.)
c. about 10% to 50% by wt. of total mono and polyhydric alcohols (preferably the minimum concentration is about 15 or 20% by wt. and the maximum concentration is about 30 or 25% by wt.) (preferably at least one alcohol is selected from the following compounds: glycerol, sorbitol, triethanolamine, or an alkylene glycol);
d. wherein the composition has a fracture initiation energy ($G_{ic}$) greater than 2 J/$m^2$. (Preferably the minimum fracture initiation energy has a lower limit of about 8, 12 or 16 and the maximum fracture initiation energy has an upper limit of about 24 or 20) J/$m^2$;
e. wherein the bar has a length extending along an x axis, a width extending along a y axis, and a thickness extending along a z axis, and the x, y and z axis are orthogonal to each other; and
f. wherein the bar has an exterior surface, wherein the exterior surface includes:
    i. a top surface, a bottom surface and a middle portion extending from the top to the bottom surface, (preferably wherein the each of the top surface, the middle portion and the bottom surface has the same composition);
    ii. wherein the top surface has a first profile extending along the x axis, the bottom surface has a second profile extending along the y axis, and the middle portion has a third profile normal to the z axis;
    iii. each of said first, second and third profiles independently being either linear, curvilinear or having both linear and curvilinear elements;
    iv. wherein at least two of the first, second and third profiles are different (preferably the first, second and third profiles are all different); and
    v. wherein the maximum value of the standard deviations of a Directional Variation Array of surface striations of each of the top surface, bottom surface and middle portion of the bar is each greater than 0.64 calculated via the DVA surface imaging method.

Optionally the fourth embodiment of the bar composition may contain 0 to about 30% by wt. of total amphoteric surfactant(s), 0 to about 20% by wt. of total nonionic surfactant(s), 0 to about 10% by wt. of total cationic surfactant(s), 0 to about 10% by wt. of total cationic polymer(s), 0 to about 20% by wt. of total hydrophobic structurant(s), 0 to about 30% by wt. of hydrophilic structurant(s), about 10 to 50% by wt. of total solvent(s), 0 to about 20% by wt. of total hydrophobic emollient(s) and 0 to about 25% by wt. of total humectant(s).

Preferably the fourth embodiment toilet bar has a fracture energy ($G_c$) greater than about 25 J/$m^2$. Preferably the minimum fracture energy has a lower limit of about 100, 150 or 200 and the maximum fracture energy has an upper limit of about 300 or 250.

Advantageously the bar has a yield stress greater than about 100 kPa. Preferably the minimum yield stress has a lower limit of about 200, 250 or 300 and the maximum yield stress has an upper limit of about 600, 450 or 400. Preferably at least two of the first, second or third profiles of the bar have curvilinear profiles. Preferably the first, second and third profiles are all curvilinear.

Surfactants:

Surfactants, also known as detergents, are an essential component of the inventive toilet bar composition. They are compounds that have hydrophobic and hydrophilic portions that act to reduce the surface tension of the aqueous solutions they are dissolved in. Useful surfactants include soap(s), and non-soap anionic, nonionic, amphoteric, and cationic surfactant(s), and blends thereof.

Anionic Surfactants:

The inventive toilet bar composition optionally contains one or more non-soap anionic detergent(s) (syndets) as discussed above.

The anionic detergent active which may be used may be aliphatic sulfonate(s), such as a primary alkane (e.g., $C_8$-$C_{22}$) sulfonate(s), primary alkane (e.g., $C_8$-$C_{22}$) disulfonate(s), $C_8$-$C_{22}$ alkene sulfonate(s), $C_8$-$C_{22}$ hydroxyalkane sulfonate(s) or alkyl glyceryl ether sulfonate(s) (AGS); or aromatic sulfonate(s) such as alkyl benzene sulfonate.

The anionic may also be alkyl sulfate(s) (e.g., $C_{12}$-$C_{18}$ alkyl sulfate) or alkyl ether sulfate (including alkyl glyceryl ether sulfates). Among the alkyl ether sulfate(s) are those having the formula:

$RO(CH_2CH_2O)_nSO_3M$ wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinate(s) (including mono- and dialkyl, e.g., $C_6$-$C_{22}$ sulfosuccinate(s)); alkyl and acyl taurate(s), alkyl and acyl sarcosinate(s), sulfoacetate(s), $C_8$-$C_{22}$ alkyl phosphate(s) and phosphate(s), alkyl phosphate ester(s) and alkoxyl alkyl phosphate ester(s), acyl lactate(s), $C_8$-$C_{22}$ monoalkyl succinate(s) and maleate(s), sulphoacetate(s), and alkyl glucoside(s) and the like.

Sulfosuccinates may be monoalkyl sulfosuccinates having the formula:

$R^4O_2CCH_2CH(SO_3M)CO_2M$; and

Amide-MEA sulfosuccinates of the formula;

$R^4CONHCH_2CH_2O_2CCH_2CH(SO_3M)CO_2M$

Wherein $R^4$ ranges from $C_8$-$C_{22}$ alkyl and M is a solubilizing cation.

Sarcosinates are generally indicated by the formula:

$R^1CON(CH_3)CH_2CO_2M$,

Wherein $R^1$ ranges from $C_8$-$C_{20}$ alkyl and M is a solubilizing cation.

Taurates are generally identified by formula:

$R^2CONR^3CH_2CH_2SO_3M$ wherein $R^2$ ranges from $C_8$-$C_{20}$ alkyl, $R^3$ may be H or $C_1$-$C_4$ alkyl and M is a solubilizing cation.

Monoacyl and/or diacyl C8-C18 isethionate surfactants having the general formula:

$RC—O(O)—CH_2—CH_2—SO_3M^+$ or $(RC—O(O)—CH_2—CH_2—SO_3)_2M^{++}$

Wherein R is an alkyl group having 8 to 18 carbons, and M is a mono or divalent cation such as, for example, sodium, potassium, ammonium, calcium and magnesium or other mono and divalent cations may be used. Preferably the isethionates have an average iodine value of less than 20.

Fatty Acid Soap

The inventive toilet bar may contain soap; as discussed above. The term "soap" is used here in its popular sense, i.e., the alkali metal or alkanol ammonium salts of aliphatic alkane- or alkene monocarboxylic acids preferably having about 6 to 22 carbon atoms, more preferably about 6 to about 18 or about 12 to 18 carbon atoms. They may be further described as alkali metal carboxylates of aliphatic hydrocarbons. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. The soaps may contain unsaturation in accordance with commercially acceptable standards. Excessive unsaturation is normally avoided to minimize color and odor issues.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

Inventive bars that contain synthetic anionic surfactants and that undergo extrusion or plodding prior to cutting preferably contain some soap in order to increase the plasticity and cohesiveness of the extruded mass. Preferably they contain more than 0.1, 0.5, 1 or 2% by wt.

Amphoteric Surfactants

As discussed above, one or more amphoteric surfactant(s) may be used in this invention. Amphoterics may be used to alter the lathering characteristics for enhanced consumer appeal. Also, the synergistic interaction between anionic and amphoteric surfactants that promotes clinical mildness is well known in the art.

Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$R^1—[—C(O)—NH(CH_2)_n—]_m—N^+—(R^2)(R^3)X—Y$

Where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric surfactants within the above general formula include simple betaines of formula:

$R^1—N^+—(R^2)(R^3)CH_2CO_2^-$ and amido betaines of formula:

$R^1—CONH(CH_2)_n—N^+—(R^2)(R^3)CH_2CO_2^-$

Where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$R^1—N^+—(R^2)(R^3)(CH_2)_3SO_3^-$ or $R^1—CONH(CH_2)_m—N^+—(R^2)(R^3)(CH_2)_3SO_3^-$

Where m is 2 or 3, or variants of these in which $—(CH_2)_3SO_3^-$ is replaced by $—CH_2C(OH)(H)CH_2SO_3^-$ In these formulae $R^1$, $R^2$ and $R^3$ are as discussed previously.

Amphoacetates and diamphoacetates are also intended to be covered in the zwitterionic and/or amphoteric compounds which are used such as e.g., sodium lauroamphoacetate, sodium cocoamphoacetate, and blends thereof, and the like.

Nonionic Surfactants

As discussed above, one or more nonionic surfactants may also be used in the toilet bar composition of the present invention.

The nonionics which may be used include in particularly the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

As discussed above, an optional component in compositions according to the invention is a water soluble cationic skin feel agent or polymer, such as for example cationic celluloses or Polyquaternium compounds. Suitable cationic polymer or copolymers have a molecular weight from about 1,000 to 2,000,000 and advantageously a high cationic charge density. Preferably, the cationic charge density should be at least 0.007 and higher where cationic charge density is defined as number of monovalent charges per repeat unit divided by the molar mass of repeat unit.

Exemplary cationic polymers which may be used according to the invention include Salcare® type polymers from Allied Colloids (UK), and Merquat® type polymers from Calgon.

Useful cationic polymers may also include high molecular weight, low charge density polymers such as Polymer JR-400® from Amerchol and cationic polysaccharides of the cationic guar gum class such as Jaguar series from Rhone-Poulenc which includes guar hydroxypropyltrimonium chloride. Examples include JAGUAR® C13S, which has a low degree of substitution of the cationic groups and high viscosity, JAGUAR® C15, having a moderate degree of substitution and a low viscosity, JAGUAR® C17 (high degree of substitution, high viscosity), JAGUAR® C16, which is a hydroxypropylated cationic guar derivative containing a low level of substituent groups as well as cationic quaternary ammonium groups, and JAGUAR® 162 which is a high transparency, medium viscosity guar having a low degree of substitution.

Suitable cationic polymers are JAGUAR® C13S, JAGUAR® C14S, JAGUAR® C15, JAGUAR® C17 and JAGUAR® C16 and JAGUAR® C162, especially Jaguar C13S. Low molecular weight cationic polymers with a high charge density, such as Merquat® and Salcare® types, are particularly effective in enhancing deposition, much more so than the larger, lower charge density guar gum derivatives such as Jaguar®.

Other suitable cationic polymers include cationic cellulose available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the trade name Polymer LM-200, and quaternary ammonium compounds such as alkyldimethylammonium halogenides.

Other preferred cationic compounds that are useful in the present invention include amido quaternary ammonium compounds such as quaternary ammonium propionate and lactate salts, and quaternary ammonium hydrolyzates of silk or wheat protein, and the like. Many of these compounds can be obtained as the Mackine™ Amido Functional Amines, Mackalene™ Amido functional Tertiary Amine Salts, and Mackpro® cationic protein hydrolyzates from the Mcintyre Group Ltd. (University Park, Ill.).

In a preferred skin cleansing embodiment of the invention having a hydrolyzed protein conditioning agent, the average molecular weight of the hydrolyzed protein is preferably about 2500. Preferably 90% of the hydrolyzed protein is between a molecular weight of about 1500 to about 3500. In a preferred embodiment, MACKPRO™ WWP (i.e. wheat germ amido dimethylamine hydrolyzed wheat protein) is added at a concentration of 0.1% (as is) in the bar. This results in a MACKPRO™ WWP "solids" of 0.035% in the final bar formula for this embodiment. Other cationic skin feel agents known in the art may be used provided that they are compatible with the inventive formulation.

Cationic Surfactants

As discussed above, one or more cationic surfactants may also be used in the inventive toilet bar composition. Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

Solvents

As discussed above, solvents may be advantageously used in the inventive bars, especially in concentrations effective to make the bars transparent or translucent. These agents work by reducing the dispersed phase particle size to below the wavelength of visible light, and also by refractive index matching of the dispersed and continuous phase of the toilet bar. By such means light transmission is enhanced and light scattering is reduced. Suitable solvents preferably include: triethanolamine (TEA), glycerin, sorbitol, propylene glycol, dipropylene glycol and polyethylene glycols of low (number average) MW (i.e. less than 1,500, preferably less than 500), blends thereof and the like. The addition of these ingredients is preferably combined with intensive mixing.

In the case where a solvent is added in an amount effective for the formulation to form a thin melt (1-10 cP) (measured by Brookfield viscometer for example) at a low temperature (ca. 100 C.), the formulation may be poured into molds so as to produce a cast melt bar. The resulting cast melt bar may be transparent or translucent. A preferred ingredient for such use is propylene glycol. Because they melt at a low temperature (i.e. below 100 C), such bars usually have a high liquid content at ambient temperature. This makes them highly plastic which may make the bars suitable candidates for a cutting process. Solvents may also be added to extruded bar formulations in small amounts (less than about 7%) to increase their plasticity for processing purposes or to enhance the "wet bar feel" or "slip" on use.

Structurants

As discussed above, structurants may be suitably used in the invention. Structurants are known by various names in the art (e.g. plasticizers, binders or structurants). Their function is primarily to change the physical properties of the bar—its hardness, plasticity, response to temperature or moisture, etc.—for purposes of improving processing behaviour or user acceptability rather than cleansing effectiveness. There are two primary types of structurants—hydrophilic and hydrophobic.

Hydrophilic Structurants

Hydrophilic structurants may be advantageously used in certain embodiments of the invention as discussed above. Useful hydrophilic structurant(s) preferably have a melting point of 40 C. to 100 C., preferably 45 C. to 100 C., more preferably 50 to 90 C. Generally these structurants will be at least 10% by wt. water soluble at 20 C.

Useful examples include moderately high molecular weight polyalkylene oxides and in particular polyethylene glycols or mixtures thereof. Polyethylene glycols (PEG's) which may be used may have a molecular weight in the range 1,500-20,000.

It should be understood that each product (e.g., Union Carbide's Carbowax® PEG-8,000) represents a distribution of molecular weights. Thus PEG 8,000, for example, has an average MW range of 7,000-9,000, while PEG 300 has an average MW range from 285 to 315. The average MW of the product can be anywhere between the low and high value, and there may still be a portion of the material with a MW below the low value and above the high value.

In some embodiments of this invention it is preferred to include a fairly small quantity of polyalkylene glycol (e.g., polyethylene glycol) with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use. Such high molecular weight polyethylene glycols (or any other water soluble high molecular weight polyalkylene oxides) may be used in combination with a larger quantity of other water soluble structurant such as the above mentioned polyethylene glycol(s) of molecular weight 1,500 to 10,000.

Some polyethylene oxide polypropylene oxide block copolymers melt at temperatures in the range of 40 to 100 C. and may also be used. Preferred here are block copolymers in which polyethylene oxide provides at least 40% by weight of the block copolymer. Such block copolymers may be used, in mixtures with polyethylene glycol or other polyethylene glycol water soluble structurant. In addition, there may be a mixture of lower and higher MW polyalkylene glycols as described in U.S. Pat. No. 5,683,973 to Post et al., hereby incorporated by reference into the subject application in its entirety.

It should be noted that, although they may not necessarily be used by themselves, certain water soluble adjuvant fillers may be used in combination with a water soluble structurant. Among these, for example, are included maltodextrin and similar water soluble starches. If included, these adjuvants would preferably be present at no more than about 10% by wt. of the composition.

Water Insoluble Structurants

Water insoluble structurants may also be advantageously used in certain embodiments of the invention as discussed above. These structurants should preferably have a melting point in the range 40-100 C., more preferably at least 50 C., notably 50 C. to 90 C. Suitable materials include fatty acids, particularly those having a carbon chain of 12 to 24 carbon atoms. Examples are lauric, myristic, palmitic, stearic, arachidonic and behenic acids and mixtures thereof and the like. Sources of these fatty acids are coconut, topped coconut, palm, palm kernel, babassu and tallow fatty acids and partially or fully hardened fatty acids or distilled fatty acids and the like. Other suitable water insoluble structurants include alkanols of 8 to 20 carbon atoms, particularly cetyl alcohol. These materials generally have a water solubility of less than 5 g/liter at 20 C. Other useful materials include triglyceride and fatty acid derivatives. These might include but are not limited to polyol esters (glyceryl monostearate and monolaurate, sorbitan stearate, glyceryl distearate) and also hydrogenated castor oil. Paraffin wax and microcrystalline wax might also be used for structuring purposes.

The relative proportions of the water soluble structurants and water insoluble structurants govern the rate at which the bar wears during use. The presence of the water insoluble structurant tends to delay dissolution of the bar when exposed to water during use and hence retard the rate of wear.

Skin Conditioning Agents

Skin conditioning agents such as non-occlusive hydrophilic emollients or humectants that soften the skin (stratum corneum) and/or occlusive hydrophobic emollients that keep it soft by retarding water loss may be advantageously used as discussed above.

Humectants such as polyhydric alcohols, e.g. glycerin and propylene glycol, and the like; polyols such as the polyethylene glycols listed below, and the like and hydrophilic plant extracts may be used.

Useful hydrophobic emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic plant extracts;

(e) hydrocarbons such as liquid paraffin, petrolatum, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grape seed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geranial, evening primrose, camphor, thymol, spirantol, penene, limonene and terpenoid oils; and (j) mixtures of any of the foregoing components, and the like.

Miscellaneous Ingredients

In addition, the toilet bar composition of the invention may include 0 to about 15% by wt. optional ingredients as follows: sequestering agents, such as tetrasodium ethylenediaminetetraacetate (EDTA), EHDP or mixtures in an amount of about 0.01 to 1%, preferably about 0.01 to 0.05%. Perfumes may be included at levels of less than about 2, 1, 0.5 or preferably less than about 0.3, 0.2 or 0.1% by wt. The compositions may further comprise preservatives such as dimethyloldimethyl hydantoin (Glydant XL1000), parabens, sorbic acid etc., and the like. The compositions may also comprise coconut acyl mono- or diethanol amides as suds boosters and strongly ionizing salts such as sodium chloride and sodium sulfate and sodium isethionate may also be used to advantage. Antioxidants such as, for example, butylated hydroxytoluene (BHT) and the like may be used advantageously in amounts of about 0.01% or higher if appropriate.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

A qualitative cuttability assessment of various formulations that differed in plasticity and hardness was performed and is summarized in Tables 1 and 2 below. Inventive bars that could be suitably shaped over three dimensions via cutting without noticeable surface imperfections to a user of the bar were unexpectedly found to have a minimum hardness level as indicated in Table 1 and a specific range of plasticity as indicated in Table 2. Physical properties provided herein were measured at nominal cutting temperatures: 40° C. for the extruded bars and 23.5° C. for melt cast sample 555. Only freshly prepared or reprocessed bars were analyzed since a comparison of the water levels and hardness (i.e. yield stress) of aged bars (i.e. where the bars were stored at least six months at ambient conditions e.g. 20 to 25 C and 30 to 70% RH) showed that aging results in both water loss and a concomitant increase in hardness of the bar.

TABLE 1

Effect of hardness and water content on cuttability of various freshly prepared or reprocessed bar formulations (1)

| sample | description | % H2O | $\sigma_y$ (kPa) | Cuttability assessment (2) |
|---|---|---|---|---|
| 555 | Cast bar(3) | 13.0 | 260 | Cuttable with Smooth appearance |
| 553 | Lux ® + 20% sunflower seed oil | 13.3 | 65 | Uncuttable - Chunks were torn out. Excessively soft and lacked cohesion |
| 543 | Dial ® | 11.9 | 462 | Uncuttable - Very brittle and tended to shatter rather than cut cleanly. |
| 551 | White Dove ® | 5.2 | 498 | Hard but cuttable |
| 549 | Lux Cream Perfection ® | 16.0 | 306 | Hard but cuttable |
| 547 | Irish Spring ® | 10.1 | 180 | Acceptable |
| 545 | Lux Marine Massage ® | 13.2 | 360 | Acceptable |

(1) Formulations are provided below. Bars were tested within 2 weeks of being processed through the plodder and cut. Bars obtained from sources other than Unilever were reprocessed as described below. The properties of the re-extruded billets and re-stamped bars are roughly comparable but should not be considered identical to freshly manufactured material that has not been reprocessed.

(2) The order of cuttability, from least cuttable (i.e. having a high level of noticeable imperfections) to most cuttable (i.e. having no noticeable imperfections) was determined to be in the following sample order: 553 < 543 < 551 < 549 < 547 < 545 < 555

(3) Melt cast soap bar made in the laboratory using the procedure described below.

Dove ® is available from Unilever HPCNA

Lux ® Cream Perfection ™ was obtained from Unilever Brazil (Gessy Lever)

Lux ® Marine Massage ™ was obtained from Unilever Brazil (Gessy Lever)

Dial ® is a product of Henkel/Dial Corp.

Irish Spring ® is a product of Colgate-Palmolive Co.

Figure 2A:
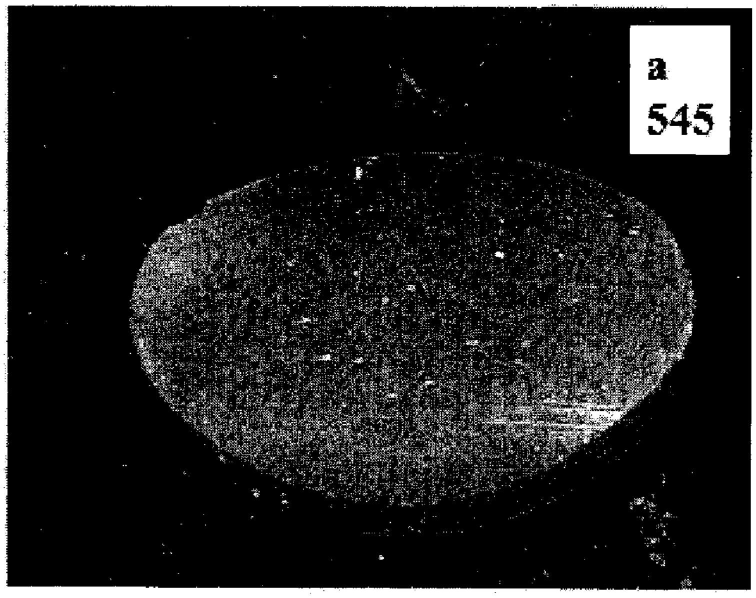
FIG. 2A is a side perspective photographic view of inventive bar sample 545.
Figure 2B:
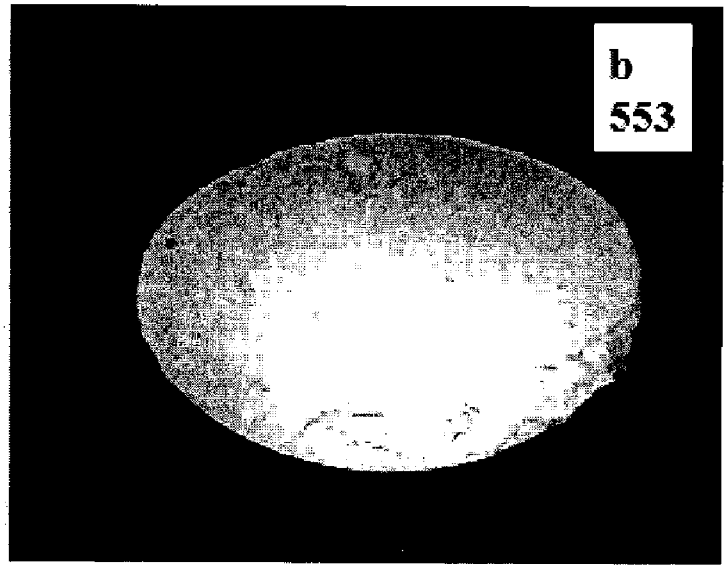
FIG. 2B is a top plan photographic view of comparative bar sample 553.

Lux ® + 20% sunflower oil" is 85/15 soap (from Gessy Lever) with 20% added sunflower oil Examples of acceptable cut and unacceptable cut bars are shown in FIGS. 2A and 2B respectively. The acceptable bar (545) had crisp edges and smooth surfaces (a slight gap appearing on the upper edge is an artifact from testing), whereas the unacceptable bar (553) had very indistinct edges, and large chunks of material were noticeably missing from its surfaces.

It was unexpectedly discovered that the material property range for satisfactory cutting (i.e. within the inventive range of plasticity and optionally hardness) substantially overlaps the corresponding range for the conventional stamping process with some surprising differences. The cuttability range appears to encompass certain soft/sticky formulations in the relatively soft 100-200 kPa yield stress range that cannot satisfactorily be stamped, whereas the stamping range is observed to include hard/brittle formulations that would likely break thin cutting wires or deform thin cutting blades of commercially available or equivalent cutters (such as e.g. the multi-station rotary table for cutting vegetables available from Forsfood OY located in Kauhajoki, Finland and described in PCT publication WO 03/086111 published on Oct. 23, 2003 and incorporated herein by reference); or cutting devices for non-soap deodorant sticks described in e.g. U.S. Pat. Nos. 5,083,486 and 6,024,967, incorporated herein by reference.

The bars tested had the following approximate composition (all values are given in weight %):

Sample 551: 50 sodium cocoyl isethionate, 20 palmitic-stearic acid, 7 82/18 tallow/coco soap, 5 water, 5 sodium isethionate, 3 coconut fatty acid, 3 sodium stearate, 3 cocamidopropyl betaine, 1 perfume, 0.2 sodium chloride, 0.2 TiO2, 0.02 EHDP, 0.02 EDTA, 0.008 BHT, 2 misc.

Sample 549: 73 anhydrous 85/15 tallow/coco soap, 18 water, 0.7 NaCl, 0.04 EDTA, 0.02 EHDP, 6 glycerine, 0.5 palm kernel fatty acid, 0.3 $TiO_2$, 0.02 whitening agent, 1 perfume, 0.1 misc.

Sample 545: 69 anhydrous 85/15 tallow/coco soap, 14 water, 1 NaCl, 0.04 EDTA, 0.02 EHDP, 4 glycerine, 1 palm kernel fatty acid, 0.02 whitening agent, 1 perfume, 1.5 propylene glycol, 6.0 sorbitol, 2 triethanolamine, 0.0002 color, 0.8 bentonite.

Sample 553: 67 anhydrous 85/15 tallow/coco soap, 13 water, 20 sunflower seed oil.

Sample 543: soap, water, PEG-6 methyl ether, palm/coconut/tallow fatty acid, perfume, glycerine, sorbitol, sodium chloride, pentasodium pentetate, tetrasodium etidronate, color, triclosan.

Sample 547: Soap (Sodium Tallowate, Cocoate, Palm Kernelate), Water, Stearic Acid, Coconut and/or Palm Kernel Acid, Glycerin, PEG 12, Fragrance, Sodium Chloride, Titanium Dioxide, Triclocarban, Pentasodium Pentetate, BHT, Ultramarine Blue Sample 555: Lab made melt cast bar: Anhydrous 80/20 POS/PKO soap 39%, glycerine 11%, ethanol 13%, sucrose 20%, water 17%.

Processing Methods

Commercially available bar samples were reprocessed by being cut up and fed into the top stage of a Mazzoni pilot scale duplex plodder with vacuum chamber (model M-150, available from Mazzoni Corso Sempione 21052 Busto Arsizio, Varese, Italy). The soap mass was homogenized by recycling it a minimum of three times at standard operating conditions of 10-15 rpm, 15° C.-20° C. cooling water on barrel, refiner plate with 1 cm holes backed by a 4-mesh screen. Once the formulations were sufficiently homogenized, they were passed through both stages with at least 18" (457 mm Hg) vacuum in the chamber and extruded as a continuous rectangular billet. The billet was cut with a hand-held wire cutter into individual blanks.

Although not wishing to be bound by the following theory, it is believed that the processes described above that were used to generate the billet did not substantially affect the ultimate properties of the bar because a minimum amount of work (in the form of shearing flow, extensional flow, optionally aided by slight heating) was used to form a homogeneous plastic mass out of the discrete pieces of soap stock. It was further observed that additional work beyond that minimum amount, using the types of equipment exemplified above, does not significantly change the physical properties of the billet.

Once the billets were produced, one-half of these were stamped immediately in a pneumatic pilot scale bar stamping machine such as a Binacchi model USN100, available from Binacchi, (Varese, Italy).

The remaining half of the billets were trimmed into an oval shape with a cookie-cutter like hand press, and cut on both sides. The cutting speed was between 10 and 60 cm/sec using a steel wire of 0.040 mm in diameter.

Toilet bar blanks that had cooled excessively were rewarmed in a microwave oven (Hot Point Model # RE965-002, Serial # DR906051R, Power: 125 KW—20 sec setting, Power Level: 10) until they reached 40° C. before being cut to prevent hardened billets from breaking the steel cutting wire employed. Plasticity and hardness properties were also measured at 40° C. for extruded bars. As noted below, the melt cast formulation was cut at ambient temperature (approx. 23.5° C.) and its physical properties were therefore measured at that temperature.

Sample 555 is a melt cast formulation and so cannot be extruded by the conventional extrusion process. Instead the soap mass was mixed in a 3000 mL Esco-Labor glass vessel. The glass vessel was equipped with an anchor blade mixing element with Teflon wall scrapers and also with a high speed homogenizer element. The vessel was heated by a circulating water bath feeding a heating jacket covering the sides and bottom.

A pre-mix of 329 g water, 275 g glycerine, and 500 g of sucrose was made up in a beaker, and then poured into the glass vessel. To that was added 325 g of 98% ethanol. The anchor blade was started up at a speed of 60 rpm, and the circulating water bath was turned on. At 20 minutes elapsed mixing time the sucrose went into solution as the batch temperature reached 50° C. At 40 minutes mixing time, 600 g of 80/20 soap noodles (at 9% water) were put in. The batch temperature dropped to 58° C. then came up to 70° C. at 55 minutes elapsed time. At this point, 471 g of soap noodles were added. The batch temperature dropped to 61° C. then began to rise again. The soap noodles slowly went into solution. The homogenizer was turned on intermittently at 1000 rpm for 1-2 minutes to help break up the noodles (use of the homogenizer was kept to a minimum in order to avoid foaming).

By 100 minutes elapsed mixing time, the batch temperature was 82° C., and the batch consisted of a thin, transparent, slightly yellow melt with a small amount of foam floating on top. The foam was skimmed off and found to weigh no more than 34 g (that is, no more than 1.4% of the total batch size of 2500 g). At this point the batch was judged to be complete, and it was poured out into block-shaped molds for use in cutting tests. Some of the batch was poured into rubber "flat-back" molds to make blanks for qualitative cuttability assessment described below. The blocks were placed in a freezer for two days, then taken out and allowed to stand for two weeks at room temperature (about 23.5° C.) before further testing. During this time the ethanol was observed to gradually evaporate out of the blocks, and the blocks became harder and more translucent.

FIG. 3A to F depicts graphs of force vs. displacement from the three point bending tests. The unacceptable sample 553 has neither substantial stiffness (i.e. yield stress) nor plasticity (i.e. fracture energy) as shown in table 2, so it fractures almost immediately at a very low force. Samples 547 and 545, which yielded acceptable cut bars, are very plastic, in that they tend to deform continuously rather than fracture cleanly. Sample 549 also shows some plastic behaviour, but not so much as Samples 547 and 545.

The other two formulations, Samples 551 and 543 are very stiff and brittle. They tended to fracture suddenly at high force and low displacement. Fracture is defined herein as the event where, instead of a stable crack propagating at the same rate of cutting with a blade or wire, the brittle material exhibits unstable crack propagation at a rate greater than the cutting rate, thereby causing toilet bar pieces to fracture off. That behaviour was exhibited by Sample 543. In addition the danger of breaking of relatively thin cutting wires is much greater with this type of material. Sample 551 was however found to provide acceptable shaping via cutting, notwithstanding its high hardness, apparently due to its high level of plasticity.

Figure 3A:
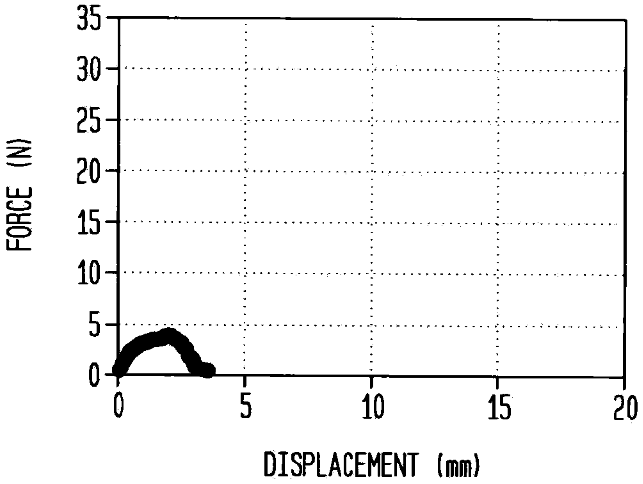
FIG. 3A is a graph depicting the relationship of Force (Newtons) vs. Displacement (mm) of the three point bending test of comparative sample 553
Figure 3B:
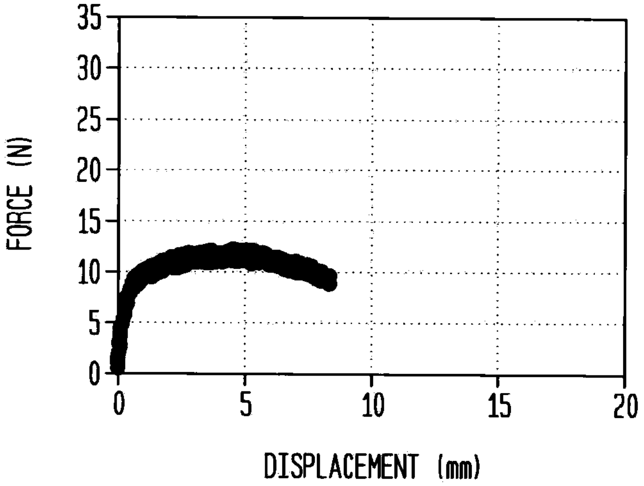
FIG. 3B is a graph depicting the relationship of Force (Newtons) vs. Displacement (mm) of the three point bending test of inventive sample 547
Figure 3C:
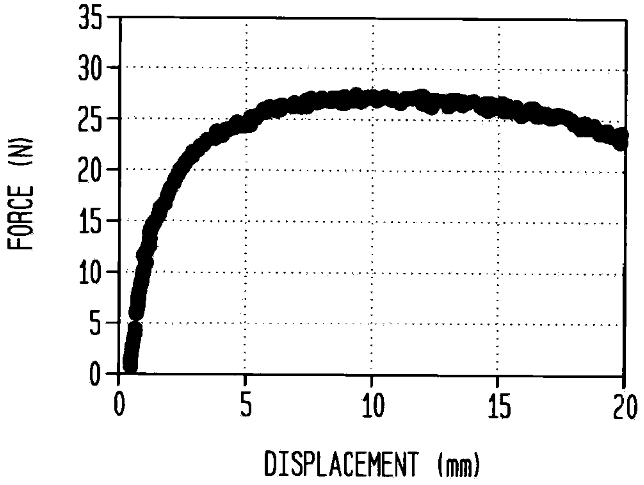
FIG. 3C is a graph depicting the relationship of Force (Newtons) vs. Displacement (mm) of the three point bending test of inventive sample 545
Figure 3D:
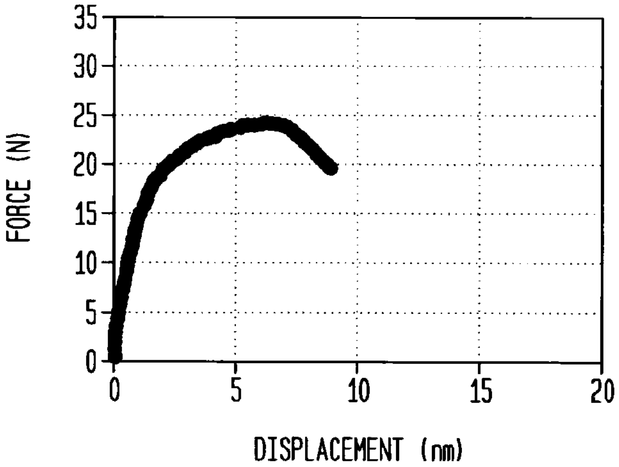
FIG. 3D is a graph depicting the relationship of Force (Newtons) vs. Displacement (mm) of the three point bending test of inventive sample 549
Figure 3E:
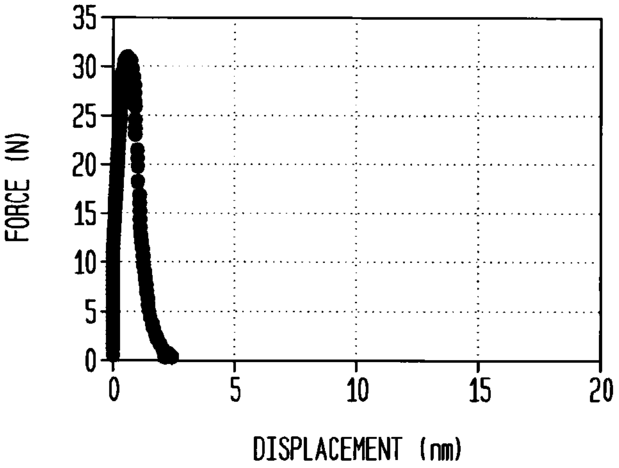
FIG. 3E is a graph depicting the relationship of Force (Newtons) vs. Displacement (mm) of the three point bending test of inventive sample 551
Figure 3F:
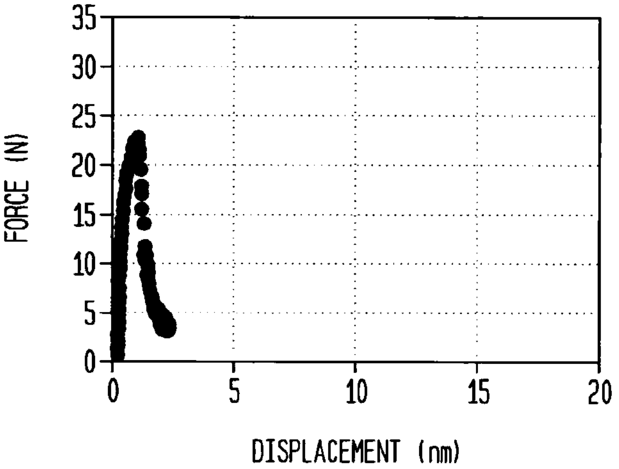
FIG. 3F is a graph depicting the relationship of Force (Newtons) vs. Displacement (mm) of the three point bending test of comparative sample 543
Figure 3G:
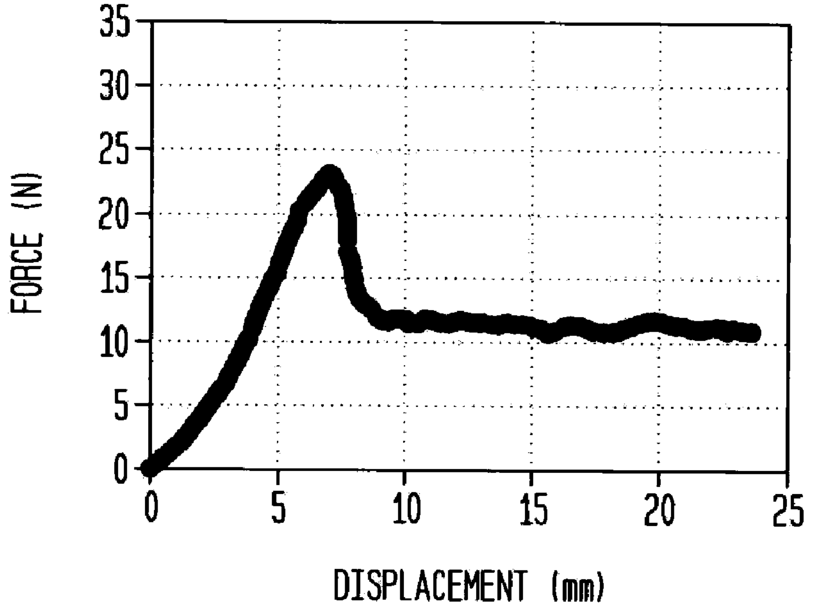
FIG. 3G is a graph depicting the relationship of Force (Newtons) vs. Displacement (mm) of the wire cutting test of comparative sample 555
Figure 4A:
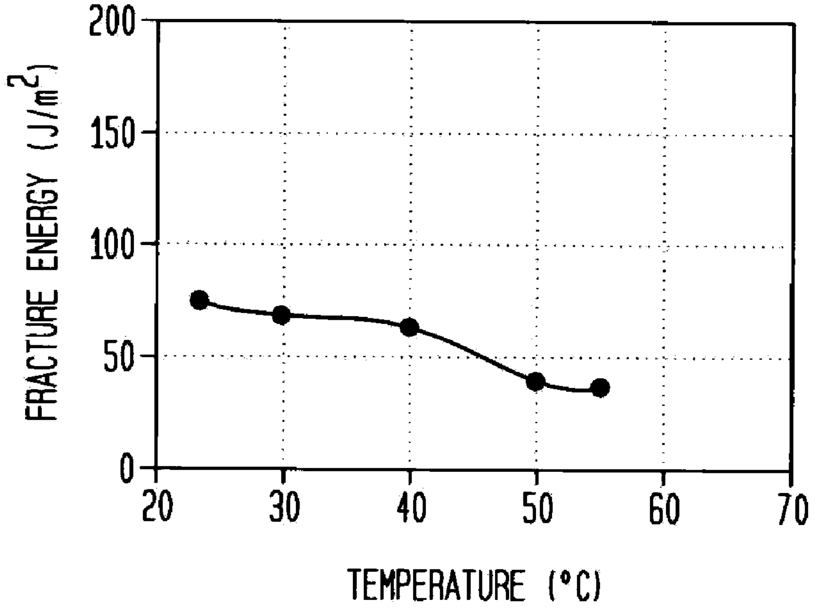
FIG. 4A is a graph depicting the relationship of fracture energy to temperature for inventive sample 551.
Figure 4B:
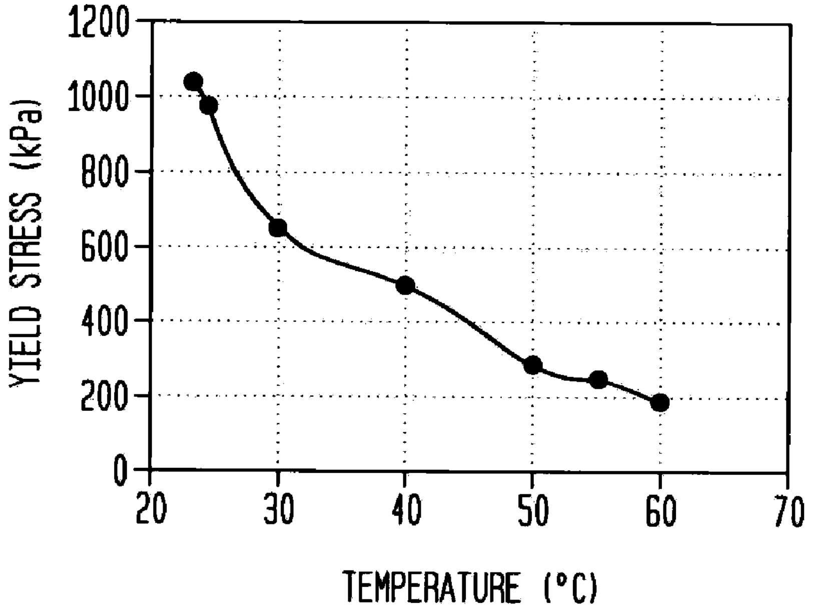
FIG. 4B is a graph depicting the relationship of yield stress to temperature for inventive sample 551.
Figure 4C:
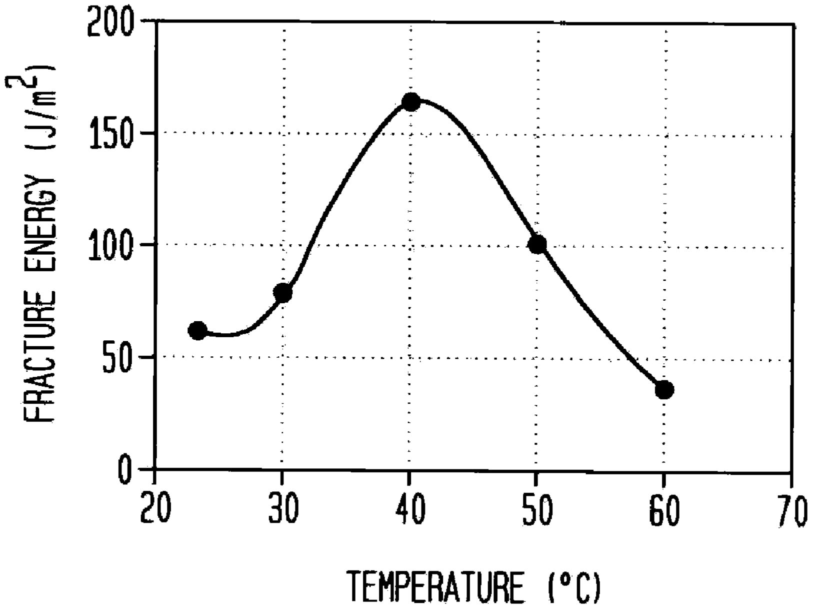
FIG. 4C is a graph depicting the relationship of fracture energy to temperature for inventive sample 549.
Figure 4D:
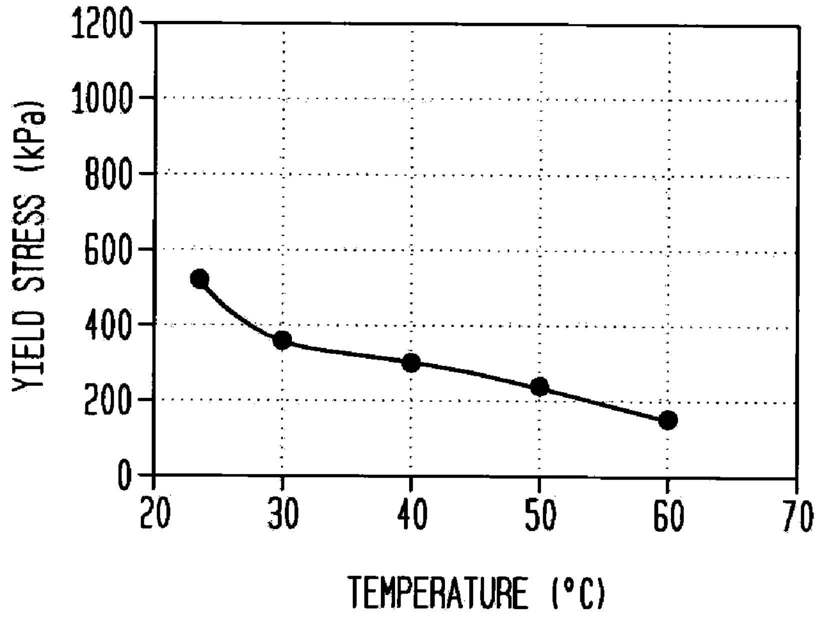
FIG. 4D is a graph depicting the relationship of yield stress to temperature for inventive sample 549.
Figure 4E:
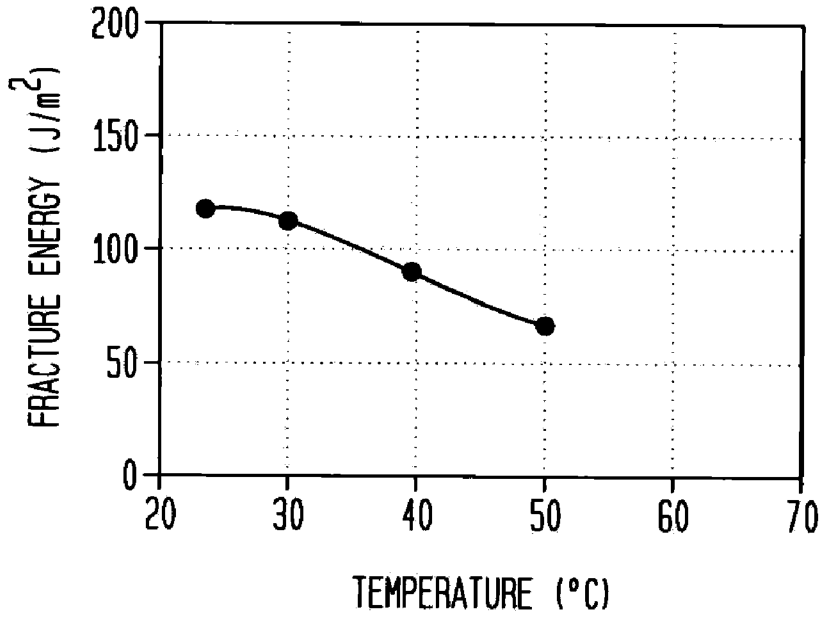
FIG. 4E is a graph depicting the relationship of fracture energy to temperature for inventive sample 555
Figure 4F:
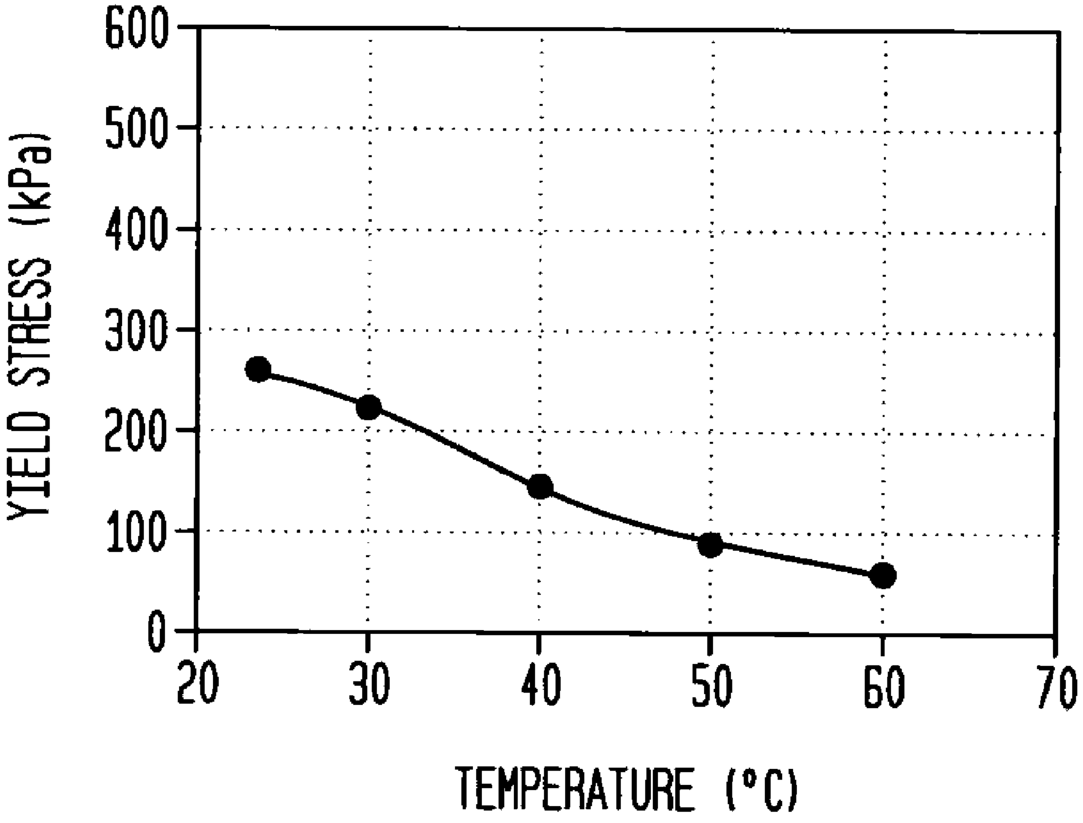
FIG. 4F is a graph depicting the relationship of yield stress to temperature for inventive sample 555

FIG. 3G depicts the wire cutting test on Sample 555, the cast formulation. In this case the force rises to a maximum ("overshoot") as the wire elastically deforms the sample surface. As the wire cuts through the interior of the sample the force drops to a "plateau" value from which the fracture energy is calculated.

Table 2 below summarizes the plasticity and yield stress parameters of the formulations described in Table 1. The plastic zone radius, fracture initiation energy, stress intensity, fracture energy, fracture stress, modulus, and bending yield stress are derived from three-point bending data of the type shown in FIG. 3A to F. The wire yield stress is from the penetrometer test described below. As discussed above, the parameters that distinguish cuttable inventive bars from uncuttable comparative bars include fracture initiation energy ($G_{ic}$) and fracture energy ($G_c$) derived from three-point bending tests. Although not wishing be bound by the following theory, it is believed that plasticity is associated with the ability to start and propagate a "stable crack" (i.e., one that propagates at the same rate the cutting element moves through the solid mass) in a solid material. Blade and wire cutting are processes whereby friction and plastic deformation forces generated by the cutting element are transferred to a stable crack. The above plasticity parameters are calculated from the area under the force vs. displacement curves of FIGS. 3A to G according to the method below (i.e. the larger the area under the curve, the greater the plasticity). The present results unexpectedly show that a specific range of plasticity is important for acceptable three dimensional shaping via cutting.

TABLE 2

Effect of plasticity and hardness on acceptable three dimensional shaping via cutting.

| parameter | units | 553 Comp. | 555 Inv. | 547 Inv. | 545 Inv. | 551 Inv. | 549 Inv. | 543 Comp. |
|---|---|---|---|---|---|---|---|---|
| plastic zone (r) | mm | 1.87 | — | 2.94 | 1.76 | 2.29 | 2.0 | 1.00 |
| fracture initiation energy ($G_{ic}$) | J/m$^2$ | 0.72 | — | 2.89 | 8.99 | 4.52 | 7.6 | 1.19 |
| stress intensity ($K_{ic}$) | kPa | 4.7 | — | 17.3 | 30.1 | 48.6 | 26.0 | 18.9 |
| fracture energy ($G_c$) | J/m$^2$ | 2.2 | 117 | 62 | 353 | 44 | 170 | 220 |
| fracture stress ($\sigma_f$) | kPa | 23 | — | 82 | 146 | 316 | 140 | 89 |
| modulus (E*) | Pa x $10^7$ | 2.0 | — | 7.8 | 7.6 | 40.0 | 6.8 | 22.4 |
| yield stress (wire) ($\sigma_y$) | kPa | 68 | 260 | 180 | 360 | 498 | 306 | 480 |

Fracture testing via three-point bending was not practicable for the cast bar (sample 555) since it would require the casting of a test billet of appropriate size to fit the test fixture. Alternatively $G_C$ was determined, based on cutting of the sample by wires of various diameters as detailed below. Although the microstructures of cast and extruded bars are very different, qualitative comparisons can still be made. The $G_C$ value for the cast bar at 23.5° C. is given in Table 2. It can be seen than the cast bar has a comparatively high plasticity.

Fracture testing via three-point bending was not practicable for the cast bar (sample 555). However an alternative method for $G_c$ is possible, based on cutting of the sample by wires of various diameters as detailed below. Although the microstructures of cast and extruded bars are very different, qualitative comparisons can be still be made. The $G_c$ value for the cast bar at 23.5° C. is given in Table 2. It can be seen than the cast bar has a comparatively high plasticity.

Another significant physical property parameter for acceptable shaping via cutting includes the yield stress ($\sigma_y$) derived from the penetrometer data as described below. In contrast to the bending test, penetrometer data can be collected for both cast and extruded samples. Yield stress was unexpectedly observed to define a lower boundary for cuttability. Yield stress is also known to be important for conventional toilet bar processing via extrusion and stamping.

The physical property parameters discussed above represent the lower boundary of cuttability. With respect to defining a practicable upper boundary for cuttability, for conventional cutting devices with wire cutting elements and/or thin blades, the upper boundary for yield stress for bars would advantageously be below the point sufficient to break the wires or deform the cutting blades. Very hard formulations would also not be practicably extrudable because of the mechanical limitations of conventional soap bar extrusion equipment. A very high $G_c$ or $G_{ic}$ would probably indicate a formulation so tough and rubbery that it would not cut to leave a smooth surface, or more likely break the cutting wires or deform the cutting blades. Therefore the lack of cuttability of such tough and rubbery bars without substantial defects as defined above or cutting implement failure (i.e. wire breakage or blade deformation) constitutes the practical upper limit for $G_c$ or $G_{ic}$, and it can be estimated that the upper limit on yield stress would be approx. 600 kPa and for $G_c$ approx. 1000 J/$m^2$

EXAMPLE 2

Figure 2C:
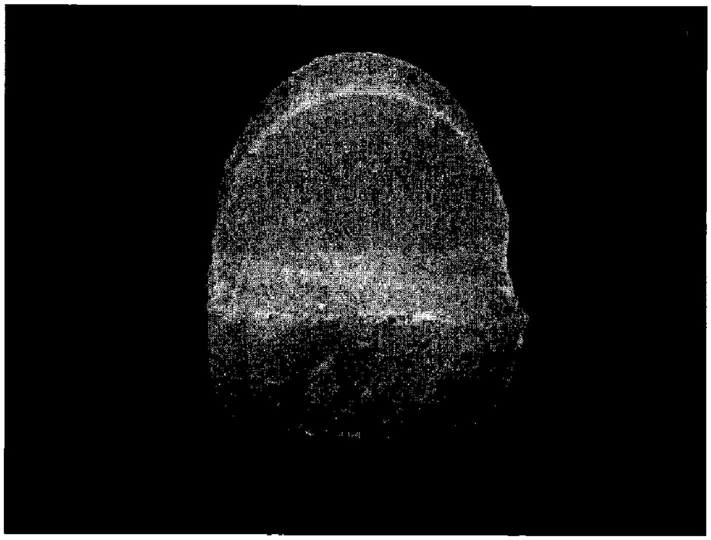
FIG. 2C is a side, perspective photographic view of inventive bar sample 555 displaying a cut section.
Figure 2D:
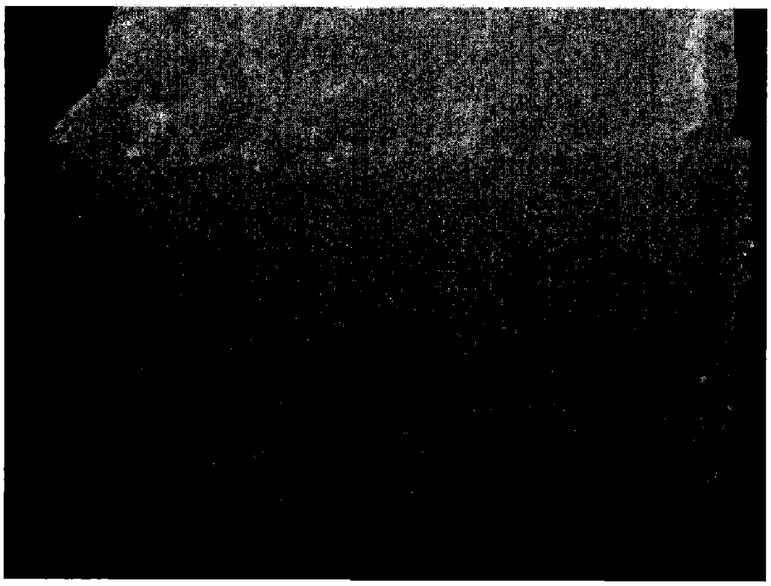
FIG. 2D is a detailed side, perspective photographic view of inventive bar sample 555 shown in FIG. 2C.
Figure 9A:
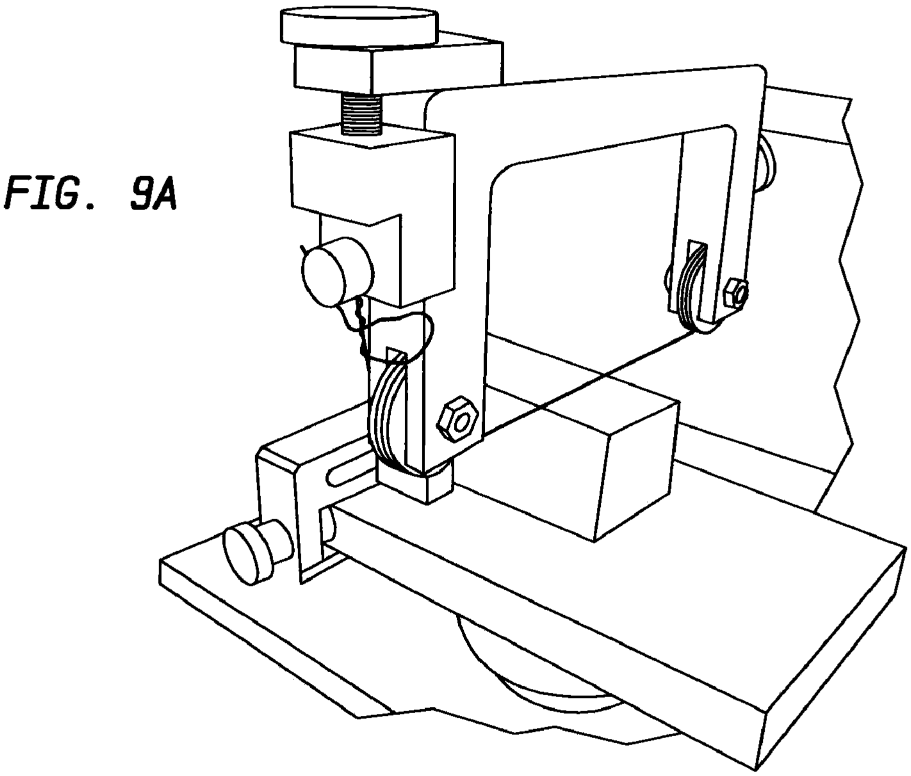
FIG. 9A is a perspective photographic view of the wire test fixture used in Example 1.
Figure 9B:
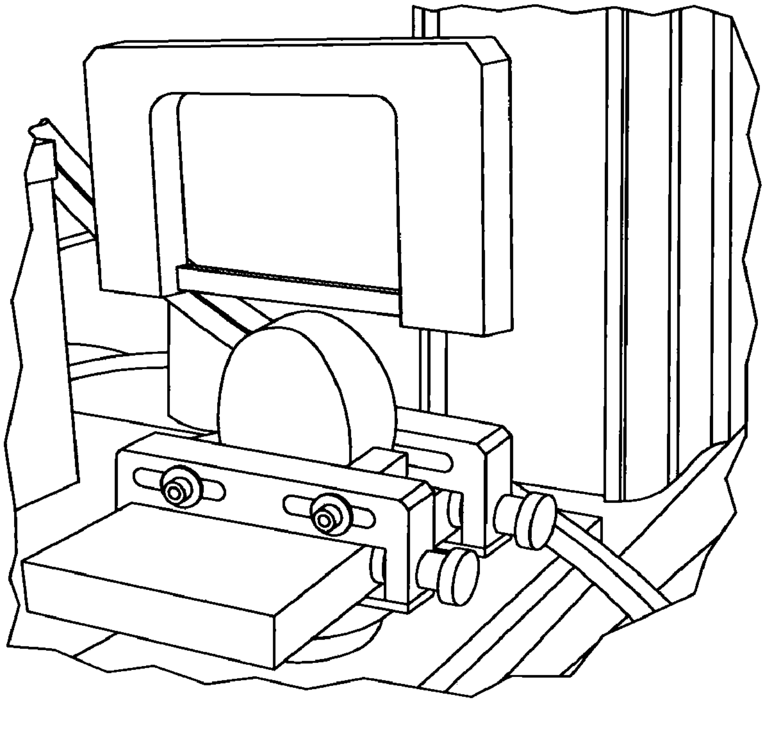
FIG. 9B is a perspective photographic view of the blade test fixture used in Example 2

Cuttability qualitative assessments were carried out on the inventive cast bar, Example 555. Bar blanks were cast in rubber "flat back" molds. The cast bar blank was removed from the mold after hardening and securely clamped in place beneath the Instron 5567 material testing machine crosshead (FIG. 9B) and cut by a steel blade (0.01 cm thick and 1.0 cm tall A2 tool steel, electroless nickel plated) having the same shape as the blade of a Mazzoni guillotine soap cutter (model TE). The blade was passed through separate bar blank samples at 50 mm/min, 100 mm/min, and 200 mm/min using the Instron machine and smooth cuts were obtained, as shown in FIG. 2C (100 mm/min sample). It was noted that cut smoothness appears to increase slightly as cutting speed increases. Similarly, a 0.020" (0.508 mm) wire was passed through separate cast bar blanks at 50 mm/min, 100 mm/min, and 200 mm/min (FIG. 9A). Again, smooth cuts were obtained as shown in FIG. 2E (200 mm/min sample). As with the blade tests, the wire cut quality appeared slightly better at higher cutting speeds.

EXAMPLE 3

The effect of toilet bar temperature on the plasticity $G_c$, $G_{ic}$, and yield stress $\sigma_y$ parameters was studied and is summarized in Tables 3, 4, and 5. The temperature dependence of $G_c$ and $\sigma_y$ are depicted graphically in FIGS. 4A to F. It was found that the temperature dependence varies with both the specific formulation used and also whether the bar is an extrudable syndet or soap based bar, or is a cast bar. As used herein, syndet based bar means that the synthetic non-soap anionic surfactant(s) constitute the majority of the total anionic surfactant content of the bar and soap based bar means that the soap(s) constitute the majority of the total anionic surfactant content of the bar.

In the processing range used (40° C.-60° C.), the plasticity ($G_c$) of soap based Sample 549 decreased significantly (from 166 to 38 J/$m^2$, or 77%) but the decrease in hardness ($\sigma_y$) was less (47%), whereas with syndet based Sample 551 it was the hardness (60%) that decreased more than the plasticity (42%). Also, the absolute plasticity of the 549 sample is much higher. The relationship between composition and its plasticity and yield stress dependence on temperature may be usefully exploited to select the optimum temperature for cutting a particular bar composition. The cast bar (FIGS. 4E and 4F) was softer than the extruded soap and syndet based bar samples discussed above. Its yield stress displayed strong temperature dependence. Even though it is soft, its fracture energy profile is similar to the much harder syndet based formulation. This, in combination with their homogeneous microstructure and high liquid content, makes cast bars surprisingly well suited for the cutting process.

TABLE 3

Temperature Effect on Fracture Parameters of Sample 549

| T, ° C. | Modulus, E* (Pa x $10^7$) | Yield stress, $\sigma_y$ (wire) (kPa) | Fracture stress, $\sigma_f$ (kPa) | Fracture energy (J/$m^2$) | Stress intensity, $K_{ic}$ (kPa) | Fracture initiation energy, $G_{ic}$ (J/$m^2$) | Plastic zone radius, r (mm) |
|---|---|---|---|---|---|---|---|
| 23.5 | 14.6 | 512 | 210 | 63 | 37.4 | 7.16 | 2.14 |
| 30 | 11.9 | 360 | 191 | 79 | 38.2 | 9.18 | 2.24 |
| 40 | 6.8 | 304 | 140 | 166 | 26.2 | 7.55 | 1.96 |
| 50 | 5.0 | 240 | 119 | 103 | 25.3 | 9.51 | 2.20 |
| 60 | 4.3 | 162 | 77 | 38 | 15.4 | 4.12 | 0.91 |

TABLE 4

Temperature Effect on Fracture Parameters of Sample 551

| T, ° C. | Modulus, E* (Pa x $10^7$) | Yield stress, $\sigma_y$ (wire) (kPa) | Fracture stress, $\sigma_f$ (kPa) | Fracture energy (J/$m^2$) | Stress intensity, $K_{ic}$ (kPa) | Fracture initiation energy, $G_{ic}$ (J/$m^2$) | Plastic zone radius, r (mm) |
|---|---|---|---|---|---|---|---|
| 23.5 | 58.4 | 1025 | 556 | 76 | 84.5 | 9.18 | 2.01 |
| 30 | 56.1 | 646 | 465 | 70 | 71.8 | 6.88 | 1.95 |
| 40 | 44.4 | 498 | 367 | 64 | 60.8 | 6.25 | 2.71 |
| 50 | 22.9 | 294 | 175 | 40 | 27.4 | 2.46 | 1.96 |
| 55 | 16.9 | 198 | 130 | 37 | 23.1 | 2.12 | 2.86 |

TABLE 5

| Temperature Effects on Parameters of Sample 555 | | |
|---|---|---|
| T, ° C. | Yield stress, $\sigma_y$ (wire) (kPa) | Fracture energy, $G_c$ ($J/m^2$) |
| 23.5 | 260 | 117 |
| 30 | 222 | 112 |
| 40 | 146 | 89 |
| 50 | 92 | 67 |
| 60 | 62 | — |

EXAMPLE 4

A surface imaging technique was devised to obtain quantitative surface topographic data of inventive bars that were acceptably shaped over three dimensions via cutting compared to comparative bars with surfaces shaped by other processes such as by stamping and/or casting. The technique is described in further detail below. Surface topographic images of the inventive cut bar samples showed a distinctive striated pattern when compared to stamped or cast bars.

Figure 5A:
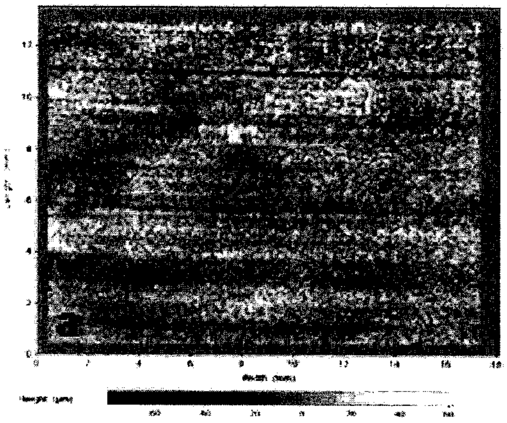
FIG. 5A is an image of the surface of inventive bar 551.
Figure 5B:
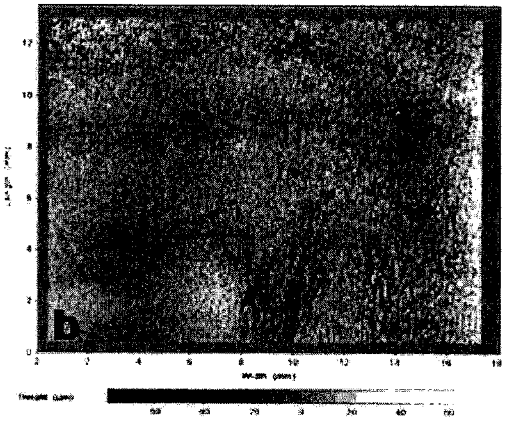
FIG. 5B is an image of the surface of a comparative version of bar 551 shaped via stamping.
Figure 5C:
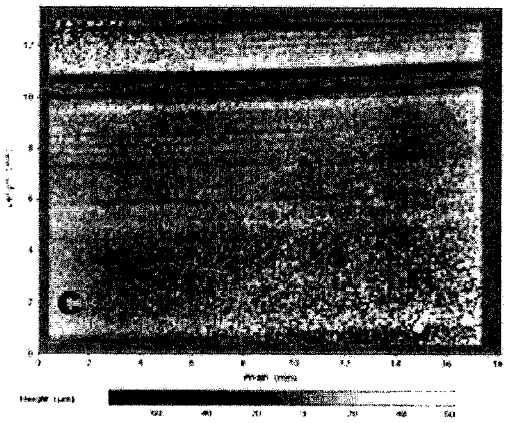
FIG. 5C is an image of the surface of inventive bar 547.
Figure 5D:
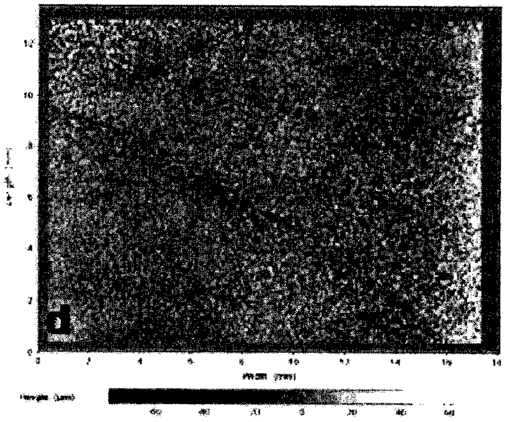
FIG. 5D is an image of the surface of a comparative version of bar 547 shaped via stamping.
Figure 6A:
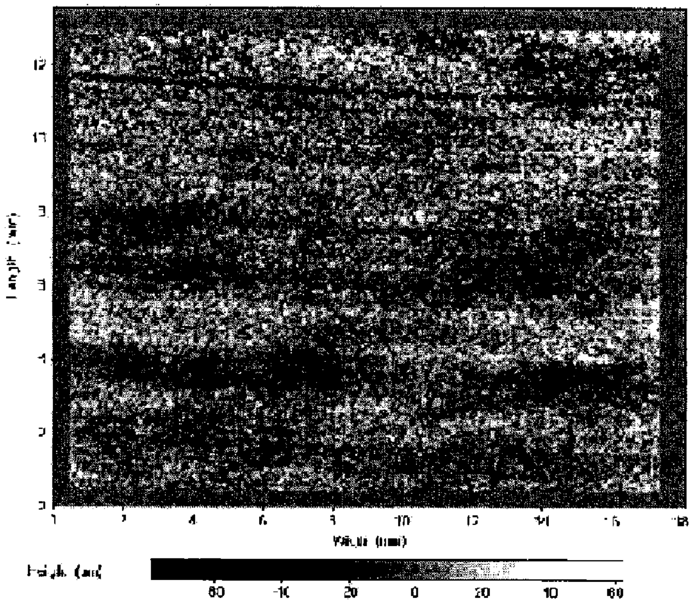
FIG. 6A is a micrographic PRIMOS input image of a representative inventive cut bar.
Figure 6B:
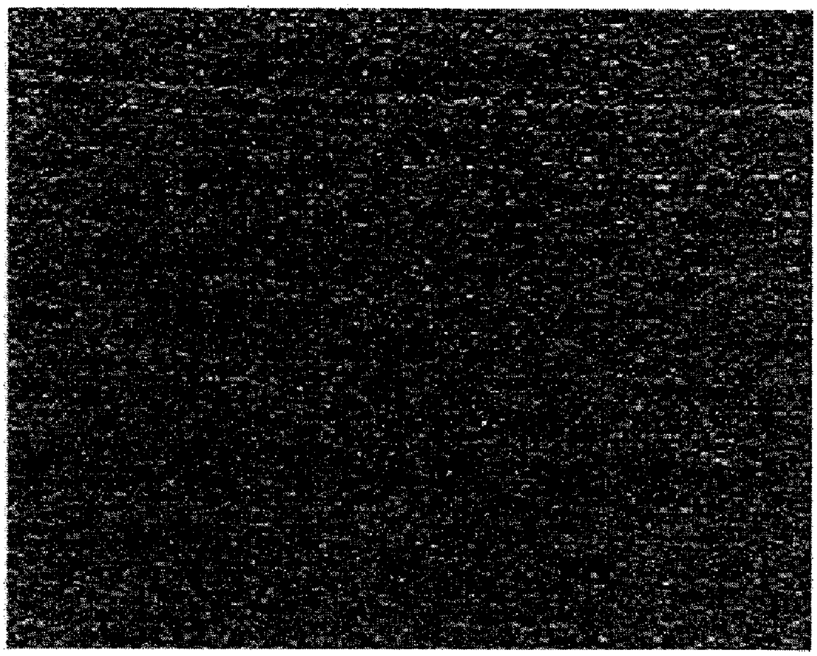
FIG. 6B is a micrographic PRIMOS image of a representative comparative stamped bar after preprocessing.

FIGS. 5A and 5B represent sample 551 that is cut and stamped respectively. Similarly FIGS. 5C and 5D represent sample 547 that is cut and stamped respectively. Sample images from cut bars and stamped bars are shown in FIG. 6A to D. It can be seen that the cut images have a distinct striated pattern. Although not wishing to be bound by the following theory, it is believed that the striated pattern is created by "stick-slip" type behaviour as stress builds up in the plastic zone ahead of the blade or wire cutting implement which is then relieved by fracturing. The inventive cut bars were found to have a maximum standard deviation in the Directional Variation Array (DVA) of greater than 0.6493 based on tests with 36 samples (18 cut and 18 non-cut) described in Table 6 below. This procedure resulted in one false positive and one false negative indication, for an overall accuracy of 95% in discriminating between inventive cut bars and comparative extruded/stamped finished bars.

TABLE 6

| Surface topographic analysis of comparative extruded and stamped vs. inventive cut toilet bars (triplicate results reported). | | |
|---|---|---|
| Sample | Process | Standard deviation in the Directional Variation Array (DVA) - Sigma |
| 543 | Extruded/stamped | 0.24668 |
| 543 | Extruded/stamped | 0.37653 |
| 543 | Extruded/stamped | 0.39259 |
| 551 | Extruded/stamped | 0.15849 |
| 551 | Extruded/stamped | 0.23867 |
| 551 | Extruded/stamped | 0.19471 |
| 547 | Extruded/stamped | 0.25705 |
| 547 | Extruded/stamped | 0.38402 |
| 547 | Extruded/stamped | 0.36704 |
| 549 | Extruded/stamped | 0.32236 |
| 549 | Extruded/stamped | 0.43121 |
| 549 | Extruded/stamped | 0.51316 |
| 545 | Extruded/stamped | 0.28171 |
| 545 | Extruded/stamped | 0.41736 |
| 545 | Extruded/stamped | 0.29796 |
| 553 | Extruded/stamped | 0.53953 |
| 553 | Extruded/stamped | 0.34268 |
| 553 | Extruded/stamped | 0.36064 |
| 543 | Cut | 3.0619 |
| 543 | Cut | 2.86 |
| 543 | Cut | 2.6792 |

TABLE 6-continued

| Surface topographic analysis of comparative extruded and stamped vs. inventive cut toilet bars (triplicate results reported). | | |
|---|---|---|
| Sample | Process | Standard deviation in the Directional Variation Array (DVA) - Sigma |
| 551 | Cut | 2.0745 |
| 551 | Cut | 2.7723 |
| 551 | Cut | 2.3054 |
| 547 | Cut | 3.8325 |
| 547 | Cut | 3.8804 |
| 547 | Cut | 4.0073 |
| 549 | Cut | 1.2291 |
| 549 | Cut | 0.80497 |
| 549 | Cut | 1.0379 |
| 545 | Cut | 1.775 |
| 545 | Cut | 0.86982 |
| 545 | Cut | 0.75907 |
| 553 | Cut | 2.6179 |
| 553 | Cut | 3.1806 |
| 553 | Cut | 3.104 |

Test Methods:

Penetrometer:

The penetrometer test measures yield stress although "hardness" is the term conventionally used. In this case the test was done using a "cheese wire" or sectilometer. The apparatus and test procedure are described below.

A billet having a square cross section is placed on a support such that the edge is facing upwards. A wire of known diameter bearing a known weight is placed against the edge. The weighted wire is then released and travels into the sample, forming a wedge-shaped cut. At a specified time, the test is stopped and the distance across the bottom of the cut section is measured.

For a viscoplastic material like toilet soap, the deformations generated by the penetrometer are related to yield stress. The principle of the measurement is that a wire penetrating into a material with a constant force will come to rest when the resistance to the wire due to sample yield stress balances the applied weight.

For the sectilometer, yield stress is given by $$\sigma_y = \frac{3}{8}\frac{F}{A}$$

Where

- F is the force (weight) bearing on the wire, which is applied Weight (in grams) multiplied by the acceleration of gravity, 980 $cm/sec^2$
- A is the projected area (diameter of wire×length of cut section)

The factor of ⅜ can be derived theoretically from the Tresca yield criterion (See e.g. Johnson, K. L., Contact Mechanics, Cambridge University Press, 1985)

The sectilometer used in this work has a 20 gauge (0.020", 0.508 mm) wire. 200 or 400 g weights are normally used, depending on the hardness of the sample. The test time is 1 minute.

Sample Calculation:

A 400 gram weight is used on the yield stress device and a 22 mm slice was measured where the wire had cut the sample after 1 minute. The yield stress is therefore:

$$\frac{(3/8)(400)\,[\text{g}]\ 9.8\ [\text{m/sec}^2]\,10^{-3}\ [\text{kg/g}]}{22\,[\text{mm}]\,0.508\ [\text{mm}]\,10^{-6}\,[\text{m}^2/\text{mm}^2]} = 131{,}532\ \text{Pa or}$$

132 kPa

Three-point Bending:

The plasticity (or brittleness) of the different formulations was measured using the following Three-Point Bend Test. An Instron 5567 material testing machine with the three-point bend rig attachment was used to obtain force vs. displacement data. The three-point bend test rig, mounted on the Instron 5567 machine, consisted of a hemispherical indenter and two static hemispherical supports. The span distance between the supports was 6 inches.

Three types of three-point bend test measurements were needed for each sample in order to obtain the fracture parameters: un-notched bar, notched bar, and indentation tests as described below. Six un-notched, four notched, and two indentation tests were run for each sample.

Rectangular billets of the same material as used for the yield stress measurements were extruded, wrapped in plastic, and equilibrated in an oven for approx. 16 hours at specified temperatures. The usual oven temperature is 40° C., as in Table 2. However, the oven can optionally be set to other temperatures to study temperature effects on fracture parameters, as in Tables 3 and 4.

After the equilibration period, test billets were removed from the oven and individually placed on the static supports of the test rig. For the un-notched test, the indenter was set in a position above the sample and then set automatically in motion as a 5 mm/min speed until the billet fractured. The notched test was carried out in the same way, except that a wedge-shaped notch approximately 0.7 cm in depth was cut in the underside of the sample opposite to the indenter. For the indentation test, the soap sample was placed on a flat surface and the hemispherical indenter was lowered onto it at a speed of 1 mm/min. The test was stopped with the force exceeded the peak force obtained from the un-notched test. The purpose of the indentation test was to correct the nominal force and displacement for the crushing of the soft samples against the three hemispherical surfaces of the rig, resulting in noticeable indentations.

Force vs. displacement data were recorded for further analysis and parameter generation. The analysis of three point bending data is well known in the art and can be found in engineering treatises for example "Fracture Mechanics: Fundamentals and Applications" by T. L. Anderson, CRC Press, Boca Raton, Fla., 1995, pages 72-79, incorporated herein by reference.

A number of parameters can be derived from three-point bending measurements, depending on the specific aspects of the material behavior that are of interest, and on the assumptions made regarding the failure mechanism. The ones investigated in this work include:

Elastic Modulus:

$$E^* = \text{slope} * \left(\frac{L_b^3}{4BW^3}\right)$$

Where slope=maximum slope of un-notched curve $L_b$=distance between supports

B=billet width (breadth)

W=billet height (thickness)

E* indicates resistance to elastic deformation. A billet with a higher E* value is stiffer than a billet with a lower E*.

Units: Pa.

Yield Stress:

$$\sigma_y = \text{force} * \left(\frac{L_b}{BW^2}\right)$$

Where force=maximum force (breaking force) of un-notched billet

The yield stress indicates resistance to plastic deformation. Although not wishing to be bound by the following theoretical explanation, it is believed that an elasto-plastic material such as soap undergoes reversible elastic deformation at low forces, followed by irreversible plastic deformation and fracture as the force increases.

Units: Pa. Fracture yield stress (as distinct from wire yield stress) is used in the calculation of plastic zone radius (see below)

Fracture Stress:

$$\sigma_f = 1.5 * \text{force(notched)} * \left(\frac{L_b}{BW^2}\right)$$

Where force (notched)=maximum force (breaking force) of a notched billet

The fracture stress is the nominal resistance to fracture, as indicated by the force required to fracture a notched billet.

Units: Pa. Fracture stress values are reported as kPa for convenience.

Fracture Energy:

$$G_c = \frac{U}{B(W-a)}$$

Where

U=area under notched curve a=notch depth $G_c$ is the energy required for crack propagation leading to fracture. The higher the value of $G_c$, the more difficult it is to fracture the sample.

Units: $J/m^2$.

Stress Intensity Factor:

$K_{ic}=\sigma_f Ya^{0.5}$

Where Y="shape factor" calculated from a, $L_b$, and W (Plati, E., Williams, J. G., Polym. Eng. Sci, 15, 470 (1975)). For $L_b/W \geqq 6$, $$Y = 1.93 - \left(\frac{3.07a}{W}\right) + \left(\frac{14.53a^2}{W^2}\right) - \left(\frac{25.11a^3}{W^3}\right) + \left(\frac{25.8a^4}{W^4}\right)$$

and has a magnitude of approx. 2 for the formulations tested.

$K_{ic}$ indicates the magnitude of the stresses around a crack tip. The higher the value of $K_{ic}$, the greater the stresses.

Units: Pa. $K_{ic}$ values are reported as kPa for convenience.

Fracture Initiation Energy:

$$G_{ic} = (1 - \nu^2) * \left( \frac{K_{ic}^2}{E^*} \right)$$

where ν. is Poisson's ratio. Poisson's ratio is assumed to be 0.5, meaning that there is no change in the total billet volume during the fracture process.

The fracture initiation energy is the energy required to initiate cracking.

Units: $J/m^2$

Plastic Zone Radius:

$$r = \frac{1}{2\pi} * \left( \frac{K_{ic}}{\sigma_y} \right)^2$$

The plastic zone radius is a measurement of the size of the plastic region around the crack tip resulting from $K_{ic}$. Materials with higher r values are more ductile (plastic) than those with lower r values.

Units: m. Plastic zone radius values are reported as mm for convenience.

Measurement of $G_c$ by wire cutting:

A simplified analysis of wire cutting yields the following equation:

$$\frac{F}{B} = G_c + (1 + \mu)\sigma_y d \quad 1)$$

Where

F is force exerted on wire as it cuts through the sample

B is length of cut

μ is coefficient of friction $\sigma_y$ is yield stress d is wire diameter

Therefore a plot of normalized cutting force vs. wire diameter should be a straight line having a slope of $(1+\mu)\sigma_y$ and an intercept of $G_c$. See: Kamyab I., Chakrabarti S., Williams J. G.; Cutting Cheese With Wire; *J. Materials Sci.;* 33, 2763-2770 (1998) incorporated herein by reference in its entirety. The fixture used for the wire test is illustrated in FIG. 9A. The yoke assembly for securing and tensioning the wire fits into the crosshead of the Instron 5567 test machine. Stainless steel wires of various diameters were obtained from Malin Company (location Brook Park, Ohio). Wire diameters below about 0.03 cm were found to be impractical for use on soap billets/bars because of the tendency of the thin wire to break during the test. The upper limit of wire diameter is dependent on the particular test rig design used.

The wire test was carried out by first equilibrating billets overnight at the desired test temperature in an oven, in the same way as was done for the 3-point bending test. Billets were then taken out one at a time and attached to the base of the test rig. The wire was positioned just above the billet; then the Instron crosshead was set in motion at 10 mm/min, with data logging to a computer. The Instron was stopped when the "plateau" region in the force vs. displacement curve was reached, which was usually when the wire had penetrated halfway through the billet. Five replicate tests were run on each billet. Three wire diameters were used: 0.020" (0.508 mm), 0.032" (0.813 mm), and 0.051" (1.295 mm)" Tests were run on three wire diameters for each of four temperatures (23.5, 30, 40, and 50° C.) for a total of 60 individual tests. The width of the billet was checked at the midpoint of the depth for each test to get the F/B value (see above equation). The data were normalized to set the point of first contact between wire and billet at 0 force and 0 displacement. The normalized data were then plotted to locate the "plateau value" of the cutting force.

Surface Analysis:

A method was developed for quantitatively analyzing the surface topography of inventive and comparative skin cleansing bars, using both instrumental and image processing protocols described below.

The instrument used comprises a stripe projector, micromirrors, and digital camera.

Three dimensional scans of the bar to be tested are obtained by placement of the bar or bar segment on a stage. Visible stripe patterns are rapidly projected on the surface (<1 sec). Surface coordinates in all three dimensions are computed from the distortion of the stripe patterns and inputted to a computer for further analysis. A MATLAB algorithm (MathWorks, Natick, Mass.) was used to convert the surface patterns into feature vectors that were then inputted into a classifier routine.

Images of each bar were obtained from three different areas, each 13 mm by 18 mm. The images were loaded into a database. An ~11 mm square was placed over each image, and the area outside the square was cropped away to remove artifacts and noise that occurs at the edges. A $5^{th}$ order polynomial filter was applied to remove the waviness of the image.

All image processing was done using MATLAB software. The texture of the images was enhanced by convoluting images with a Prewitt filter flt=[1 1 1; 0 0 0; −1 −1 −1].

The filtered images were used for calculating the directional variation array (DVA). The DVA in turn forms the input for a feature vector. The three feature vectors for the three areas scanned in each bar make up the feature matrix. The procedure is as follows:

1. Pre-processing 1.1. Input: Micrographic images (1024×768 pixels) as shown in FIG. 6(*a*) were processed as described in section 1.3 below to yield an output image as shown in FIG. 6(*b*), an image of size 565×764 pixels with the horizontal texture enhanced.

1.2. Output: an image with size 565×764 pixels with the horizontal texture enhanced 1.3. Procedure 1.3.1. Cut the rectangular area of 567×766 pixels from the input image 1.3.2. Use Prewitt filter flt=[1 1 1; 0 0 0; −1 −1 −1]

1.3.3. Convolve the result of 1.3.1 with the filter in 1.3.2, take the valid range of the result with size 565×764 pixels as the output of pre-processing. Use the Matlab function conv2, the Matlab command to perform this function is outimg=conv2(inimg,flt,'valid'); where fit is the filter defined as above, and inimg and outimg are the input and output images, respectively.

2. Compute a Directional Variation Array (DVA)
2.1 Input: output from step 1.3.3.
2.2 Output: a DVA vector with length of 21
2.3 Procedure
2.3.1 Do the following steps 2.3.2 to 2.3.6 with ang=−10° to 10°
2.3.2. Rotate the pre-processed image to the angle ang, output is an image of varied size holding the rotated image with four triangle blank areas in its corners.
2.3.3 Calculate the mean along each of the line, parallel to the long axis, to get a mean array.
Note: Do not take the blank area (caused by the rotation) into the mean computation.
2.3.4 Cut off the two ends and leave the center part (of length 561 pixels) of the mean array
2.3.5 Compute the SD (standard deviation) of the mean array
2.3.6 Take the output value of 2.3.5 as the N-th element in the DVA, where N=ang+11

Figures 7A, 7B, 7C, 7D:
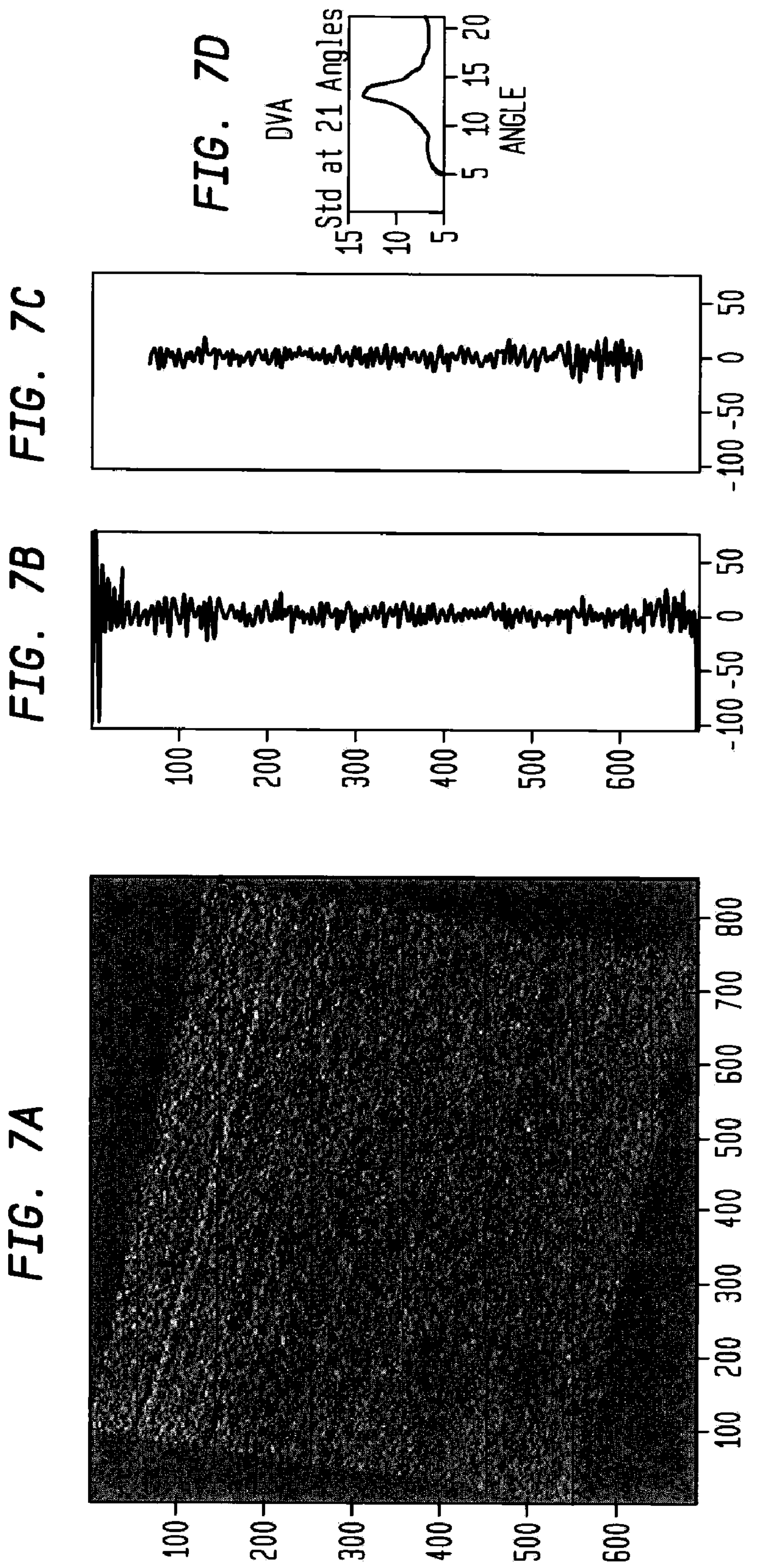
FIG. 7 shows in schematic form the steps to compute one element in the DVA from a rotated image of the same sample depicted in FIGS. 6A and B.

Steps to compute one element in the DVA array from a rotated image are shown in FIG. 7

3. Compute feature vector based on the DVA
3.1 Input: output from step 2.3.
3.2 Output: a feature vector with length of 6
3.3 Procedure
3.3.1 Feature 1=ang0 where DVA takes its maximum
3.3.2 Feature 2=maximum of the DVA
3.3.3 Feature 3=minimum of the DVA
3.3.4 Feature 4=SD of the DVA
3.3.5 Feature 5=frequency of the mean array at angle ang0 computed as follows
3.3.5.1 With angle equals ang0, re-do the steps 2.3.2, 2.3.3, and 2.3.4.
3.3.5.2 Count the number of peaks in the resulting array as the frequency. The Matlab command codes to perform this function are

```
mary(diff(mary)==0) = [ ];
peak_num = sum(diff(diff(mary)>0)==1); where
mary is the mary obtained from 3.3.5.1.
```

3.3.6 Feature 6=frequency of the smoothed mean array at angle ang0 as follows
3.3.6.1 Same as 3.3.5.1.
3.3.6.2 Smooth the obtained mean array by (1D) convolution with filter [1 1 1].

The Matlab command codes to perform this function are

```
Smoothed_mary=conv(mary,ones(3,1)); where
mary is the mary obtained from 3.3.6.1.
```

3.3.6.3 Same as 3.3.5.2.

Figure 8A:
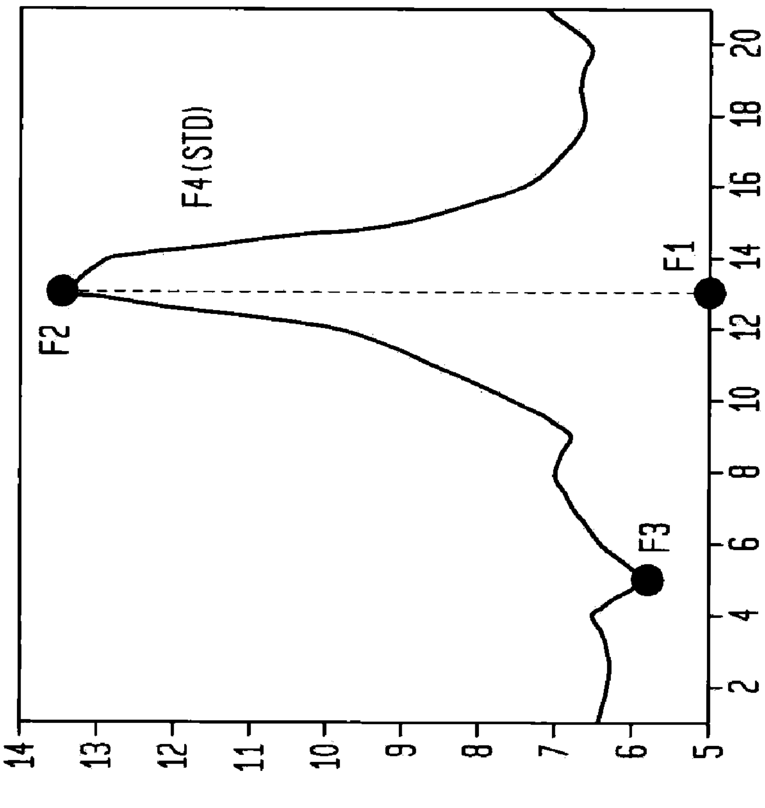
FIG. 8 shows in schematic form the steps to create a Feature Vector from one DVA of the same sample depicted in FIGS. 6A, 6B and 7.
Figure 8B:
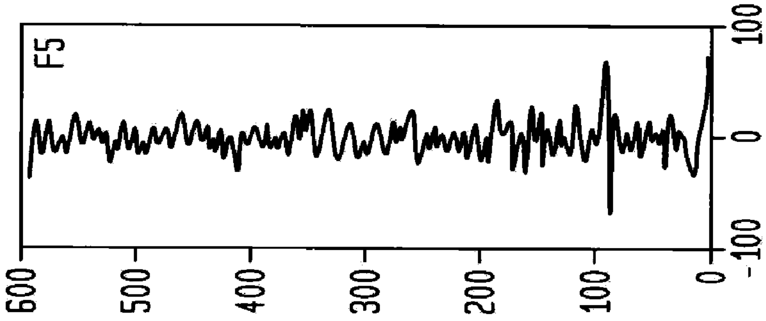
Figure 8C:
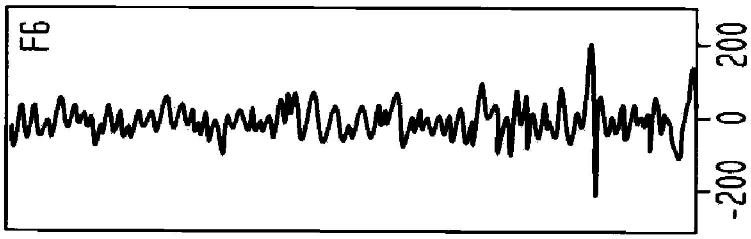

Steps to create a Feature Vector, FV=(F1, F2, F3, F4, F5, F6), from one DVA are shown in FIG. 8

4. Classification
1.4. Input: a feature matrix FM, and associated truth value array t
1.4.1. For each sample image of the soap bars, get the output from step 3.3, a row vector of length 6
1.4.2. The collection of all such feature vectors form a vector matrix, with size N×6, where N is the number of the samples. This is the input feature matrix FM.
1.4.3. t is a list (must be with length N) of 0 and 1's telling whether a sample belongs to class 0 or class 1
4.2 Output: A classifier—a rule to discriminate different sample toilet bar images
4.3 Procedure
4.3.1 Create a classification tree T for predicting response t as a function of the feature matrix FM. The Matlab function treefit, the Matlab command code to perform this function is:

```
T=treefit(FM,t,'method','classification','splitmin' ,3 ); where
FM and t are defined as above, and T is the output tree.
```

4.3.2. Analyze the tree, and decide the classifier.
4.3.2.1. View the tree with the help of the Matlab tools, the Matlab command codes to perform this function are

```
FNAMES={'peak_angle','sgm','max','min','freq1','freq2'};
treedisp(t,'names',FNAMES);
```

4.3.2.2. Examine the tree from the graphic display, each branch in the tree is labelled with its decision rule, and each terminal node is labelled with the predicted value for that node. A computer pointing device click on any node reveals more information about that node.
4.3.2.3. Ignore the lower levels of the tree if it has more than 3 levels, with the pop-up menu 'click to display' set to be 'class membership', right click the left and right nodes of the second level, to find out how much error would be caused if only the first level decision rule is used.
4.3.2.4. If the error rate is satisfied, output the rule, in the form of feature_name [> or <] critical value 5. Classifier
5.1. To determine if a soap sample was prepared by cutting or a non-cutting process such as casting or stamping the following procedure is used:
5.2. Do steps 1, 2, and
5.3. Do 3.3.4 (generally, do the step 3.3.x to compute the feature_name, as found in 4.3.2.3), and obtain a single value. If the resultant value is larger than 0.6493(generally, critical value), the sample will be classified as class 0 (inventive cut bar), otherwise it will belong to the comparative non-cut bar class.

The foregoing description and examples illustrate selected embodiments of the present invention. In light thereof variations and modifications will be suggested to one skilled in the art, all of which are within the scope and spirit of this invention.

What is claimed:

1. A shaped toilet bar comprising:
a. about 10% to 60% by wt. of total non-soap anionic surfactant(s);
b. 0% to about 30% by wt. of fatty acid soap(s);
c. wherein the bar has a fracture initiation energy ($G_{ic}$) greater than 2 J/$m^2$;
d. wherein the bar has a length extending along an x axis, a width extending along a y axis, and a thickness extending along a z axis, and the x, y and z axis are orthogonal to each other; and e. wherein the bar has an exterior surface, wherein the exterior surface includes:

i. a top surface, a bottom surface and a middle portion extending from the top to the bottom surface;

ii. wherein the top surface has a first profile extending along the x axis, the bottom surface has a second profile extending along the y axis, and the middle portion has a third profile normal to the z axis;

iii. each of said first, second and third profiles independently being either linear, curvilinear or having both linear and curvilinear elements;

iv. wherein at least two of the first, second and third profiles are different (preferably the first, second and third profiles are all different); and v. wherein the maximum value of the standard deviations of a Directional Variation Array of surface striations of each of the top surface, bottom surface and middle portion of the bar is each greater than 0.64 calculated via the DVA surface imaging method.

2. A toilet bar according to claim 1 wherein the bar has a fracture energy ($G_c$) greater than about 25 J/$m^2$.

3. A toilet bar according to claim 1 wherein the bar has a yield stress greater than about 100 kPa.

4. The toilet bar according to claim 1, wherein at least two of the first, second or third profiles have curvilinear profiles.

5. The toilet bar according to claim 4, wherein the at least two curvilinear profiles are different.

6. A shaped toilet bar comprising:

a. about 5% to 40% by wt. of total non-soap anionic surfactant(s);

b. about 30% to 80% by wt. of fatty acid soap(s);

c. wherein the bar has a fracture initiation energy ($G_{ic}$) greater than 2 J/$m^2$.;

d. wherein the bar has a length extending along an x axis, a width extending along a y axis, and a thickness extending along a z axis, and the x, y and z axis are orthogonal to each other; and e. wherein the bar has an exterior surface, wherein the exterior surface includes:

i. a top surface, a bottom surface and a middle portion extending continuously from the top to the bottom surface,;

ii. wherein the top surface has a first profile extending along the x axis, the bottom surface has a second profile extending along the y axis, and the middle portion has a third profile normal to the z axis;

iii. each of said first, second and third profiles independently being either linear, curvilinear or having both linear and curvilinear elements;

iv. wherein at least two of the first, second and third profiles are different; and v. wherein the maximum value of the standard deviations of a Directional Variation Array of surface striations of each of the top surface, bottom surface and middle portion of the bar is each greater than 0.64 calculated via the DVA surface imaging method.

7. A toilet bar according to claim 6 wherein the bar has a fracture energy ($G_c$) greater than about 25 J/$m^2$.

8. A toilet bar according to claim 6 wherein the bar has a yield stress greater than about 100 kPa.

9. The toilet bar according to claim 6, wherein at least two of the first, second or third profiles have curvilinear profiles.

10. The toilet bar according to claim 9, wherein the at least two curvilinear profiles are different.

11. A shaped toilet bar comprising:

a. 0% to about 10% by wt. of total non-soap anionic surfactant(s);

b. about 40% to 90% by wt. of fatty acid soap(s);

c. wherein the composition has a fracture initiation energy ($G_{ic}$) greater than 2 J/$m^2$;

d. wherein the bar has a length extending along an x axis, a width extending along a y axis, and a thickness extending along a z axis, and the x, y and z axis are orthogonal to each other; and e. wherein the bar has an exterior surface, wherein the exterior surface includes:

i. a top surface, a bottom surface and a middle portion extending continuously from the top to the bottom surface,);

ii. wherein the top surface has a first profile extending along the x axis, the bottom surface has a second profile extending along the y axis, and the middle portion has a third profile normal to the z axis;

iii. each of said first, second and third profiles independently being either linear, curvilinear or having both linear and curvilinear elements;

iv. wherein at least two of the first, second and third profiles are different; and v. wherein the maximum value of the standard deviations of a Directional Variation Array of surface striations of each of the top surface, bottom surface and middle portion of the bar is each greater than 0.64 calculated via the DVA surface imaging method.

12. A toilet bar according to claim 11 wherein the bar has a fracture energy ($G_c$) greater than about 25 J/$m^2$.

13. A toilet bar according to claim 11 wherein the bar has a yield stress greater than about 100 kPa.

14. The toilet bar according to claim 11, wherein at least two of the first, second or third profiles have curvilinear profiles.

15. The toilet bar according to claim 14, wherein the at least two curvilinear profiles are different.

16. A shaped toilet bar comprising:

a. 0 to about 40% by wt. of total non-soap anionic surfactant(s);

b. 0 to about 60% by wt. of fatty acid soap(s), provided that the sum of total non-soap anionic surfactants and fatty acid soaps is not 0;

c. about 10% to 50% by wt. of total mono and polyhydric alcohols;

d. wherein the composition has a fracture initiation energy ($G_{ic}$) greater than 2 J/$m^2$;

e. wherein the bar has a length extending along an x axis, a width extending along a y axis, and a thickness extending along a z axis, and the x, y and z axis are orthogonal to each other; and f. wherein the bar has an exterior surface, wherein the exterior surface includes:

i. a top surface, a bottom surface and a middle portion extending from the top to the bottom surface;

ii. wherein the top surface has a first profile extending along the x axis, the bottom surface has a second profile extending along the y axis, and the middle portion has a third profile normal to the z axis;

iii. each of said first, second and third profiles independently being either linear, curvilinear or having both linear and curvilinear elements;

iv. wherein at least two of the first, second and third profiles are different; and v. wherein the maximum value of the standard deviations of a Directional Variation Array of surface striations of each of the top surface, bottom surface and middle portion of the bar is each greater than 0.64 calculated via the DVA surface imaging method.

17. A toilet bar according to claim 16 wherein the bar has a fracture energy ($G_c$) greater than about 25 $J/m^2$.

18. A toilet bar according to claim 17 wherein the bar has a yield stress greater than about 100 kPa.

19. The toilet bar according to claim 17, wherein at least two of the first, second or third profiles have curvilinear profiles.

20. The toilet bar according to claim 19 wherein the at least two curvilinear profiles are different.

* * * * *